US011064940B2

(12) United States Patent
Saab

(10) Patent No.: US 11,064,940 B2
(45) Date of Patent: Jul. 20, 2021

(54) METHODS FOR DETECTING AND TREATING PAIN USING BRAIN ACTIVITY

(71) Applicant: Rhode Island Hospital, Providence, RI (US)

(72) Inventor: Carl Saab, Providence, RI (US)

(73) Assignee: Rhode Island Hospital, Providence, RI (US)

( * ) Notice: Subject to any disclaimer, the term of this patent is extended or adjusted under 35 U.S.C. 154(b) by 114 days.

(21) Appl. No.: 15/581,669

(22) Filed: Apr. 28, 2017

(65) Prior Publication Data

US 2017/0311882 A1 Nov. 2, 2017

Related U.S. Application Data

(60) Provisional application No. 62/329,345, filed on Apr. 29, 2016.

(51) Int. Cl.

| | |
|---|---|
| *A61K 31/138* | (2006.01) |
| *A61K 31/197* | (2006.01) |
| *A61B 5/00* | (2006.01) |
| *A61B 5/0476* | (2006.01) |
| *A61K 45/06* | (2006.01) |
| *A61B 5/369* | (2021.01) |
| *A61B 5/374* | (2021.01) |
| *A61K 31/192* | (2006.01) |
| *A61K 49/00* | (2006.01) |
| *A61N 2/00* | (2006.01) |
| *A61N 5/06* | (2006.01) |
| *A61N 5/067* | (2006.01) |

(52) U.S. Cl.
CPC ............ *A61B 5/4848* (2013.01); *A61B 5/369* (2021.01); *A61B 5/374* (2021.01); *A61B 5/4824* (2013.01); *A61B 5/7257* (2013.01); *A61K 31/138* (2013.01); *A61K 31/192* (2013.01); *A61K 31/197* (2013.01); *A61K 45/06* (2013.01); *A61K 49/0004* (2013.01); *A61N 2/006* (2013.01); *A61N 2/008* (2013.01); *A61N 5/0622* (2013.01); *A61N 2005/063* (2013.01); *A61N 2005/067* (2013.01)

(58) Field of Classification Search
CPC .. A61K 31/138; A61K 31/192; A61K 31/197; A61N 2500/067
See application file for complete search history.

(56) References Cited

U.S. PATENT DOCUMENTS

| | | | | |
|---|---|---|---|---|
| 2008/0249430 | A1* | 10/2008 | John | A61B 5/0476 600/544 |
| 2009/0252786 | A1 | 10/2009 | Hanz | |
| 2015/0367133 | A1* | 12/2015 | Schiff | A61N 1/36064 607/45 |

FOREIGN PATENT DOCUMENTS

| | | |
|---|---|---|
| WO | WO-2010/147913 A1 | 12/2010 |
| WO | WO-2011/086563 A2 | 7/2011 |
| WO | WO-2015/071901 A2 | 5/2015 |

OTHER PUBLICATIONS

Backonja et al., "Tonic Changes in Alpha Power During Immersion of the Hand in Cold Water," Electroencephalogr Clin Neurophysiol. 79(3):192-203 (1991).
Extended European Search Report for European Application No. 17790569.2, dated Mar. 16, 2020 (9 pages).
Wang et al., "Theta-frequency Phase-Locking of Single Anterior Cingulate Cortex Neurons and Synchronization With the Medial Thalamus Are Modulated by Visceral Noxious Stimulation in Rats," Neuroscience. 298:200-10 (2015).
LeBlanc et al., "Cortical theta is increased while thalamocortical coherence is decreased in rat models of acute and chronic pain," Pain. 155(4):773-82 (2014).
LeBlanc et al., "Electroencephalographic signatures of pain and analgesia in rats," Pain. 157(10):2330-40 (2016).
Levitt et al., "Electroencephalographic frontal synchrony and caudal asynchrony during painful hand immersion in cold water," Brain Res Bull. 130:75-80 (2017).
LeBlanc et al.,"Thalamic Bursts Down-regulate Cortical Theta and Nociceptive Behavior," Sci Rep. 7(1):2482 (2017).
Koyama et al., "An Electroencephalography Bioassay for Preclinical Testing of Analgesic Efficacy," Sci Rep. 8(1):16402 (2018).
Koyama et al., "Sub-paresthesia spinal cord stimulation reverses thermal hyperalgesia and modulates low frequency EEG in a rat model of neuropathic pain," Sci Rep. 8(1):7181 (2018).
Levitt et al., "Automated detection of electroencephalography artifacts in human, rodent and canine subjects using machine learning," J Neurosci Methods. 307:53-59 (2018).
Buzsáki et al., "The origin of extracellular fields and currents—EEG, ECoG, LFP and spikes," Nat Rev Neurosci. 13(6):407-20 (2012).
Dubey et al., "Cortical Electrocorticogram (ECoG) Is a Local Signal," J Neurosci. 39(22):4299-4311 (2019).
Fukushima et al., "Studying brain functions with mesoscopic measurements: Advances in electrocorticography for non-human primates," Curr Opin Neurobiol. 32:124-31 (2015).
International Search Report and Written Opinion for International Application No. PCT/US2017/030178, dated Jul. 13, 2017 (19 pages).

* cited by examiner

*Primary Examiner* — Zohreh A Fay
(74) *Attorney, Agent, or Firm* — Clark & Elbing LLP

(57) ABSTRACT

Disclosed are methods for detecting pain in a subject, such as a mammal (e.g., a human), using brain activity, e.g., as determined by electroencephalography. The methods are useful for treating or reducing the likelihood of pain in a subject by determining power amplitude from the power spectral density of the waveforms and, e.g., administering a therapeutic agent to the subject. The methods disclosed herein may also be utilized to screen for a therapeutic agent that decreases power amplitude using a non-human animal subject. The methods also feature the stimulation of thalamic reticular nucleus of a subject to treat or reduce pain.

17 Claims, 15 Drawing Sheets

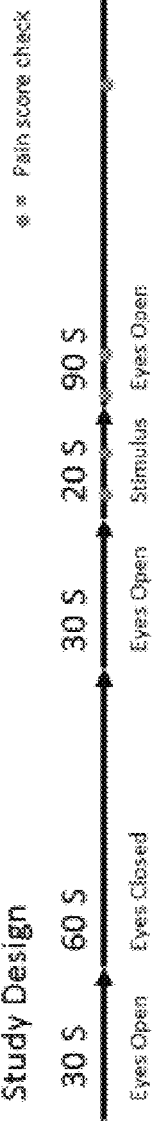
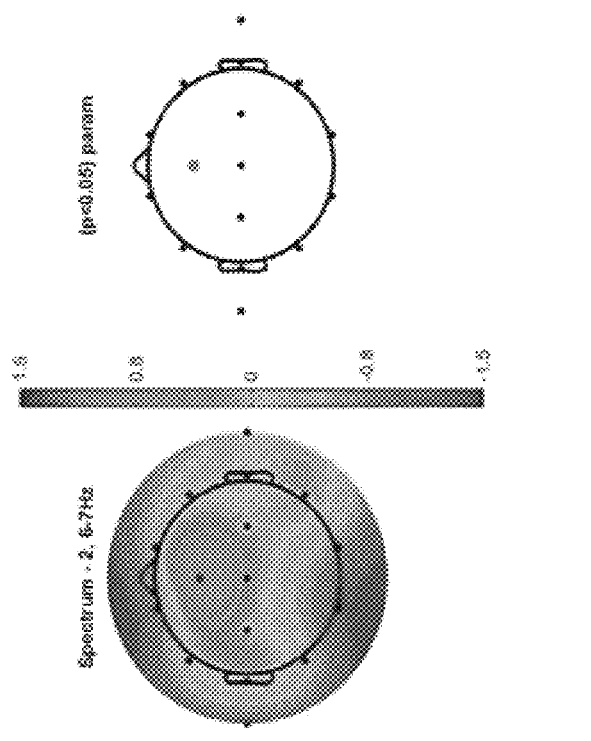
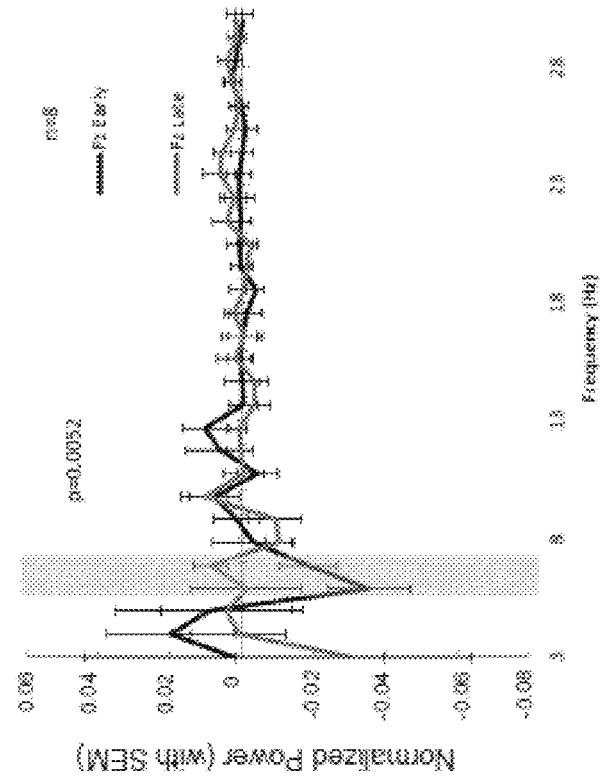
FIG. 8A
FIG. 8B
FIG. 8C

METHODS FOR DETECTING AND TREATING PAIN USING BRAIN ACTIVITY

FIELD OF THE INVENTION

The invention features methods for detecting pain using brain activity as determined by, e.g., electroencephalography (EEG), particularly for the diagnosis and treatment of pain and for screening of therapeutic agents that treat or prevent pain.

BACKGROUND

Rhythmic activity in field potentials, referred to as oscillation, is an essential mode of communication between neuronal ensembles. Recordings of brain activity invariably feature oscillation at multiple frequencies. Oscillation in the brain is thought to require cortical layer hierarchy and recruitment of subcortical structures, such as the thalamus. Neuronal oscillation plays a crucial, though as of yet incompletely defined, role in health and disorders of thought and cognition, such as autism and schizophrenia. For instance, pain modulates brain oscillation in animals, including humans. Recent studies using functional magnetic resonance imaging (fMRI) suggest that chronic pain alters functional connectivity between brain structures relevant to nociceptive processing. However, temporal resolution of fMRI (~1 Hz) is well below the frequency domain of fast neuronal 'spiking' activity (typically above 500 Hz) or neuronal oscillation related to cognition (between 2-250 Hz). Notably, animals used in fMRI studies are deeply anesthetized or head-restrained, and thus, do not reflect the physiology and different pain states of awake, freely-behaving animals.

Pain is a major symptom in many medical conditions and can significantly interfere with a patient's quality of life and general functioning. The financial burden associated with chronic pain in the United States is estimated to be greater than $150 billion a year, due to decreased productivity and medical expenses. Accordingly, there exists a need in the medical field to develop safe and effective methods of detecting pain and the use of these methods to determine efficacious therapies for the diverse diseases and disorders associated with pain. Thus, methods capable of detecting and monitoring pain are highly desirable.

SUMMARY OF THE INVENTION

Disclosed are methods to detect and treat pain in subjects (such as a mammal (e.g., a human)) using brain activity, e.g., as determined by electroencephalography (EEG). Additionally, methods of screening for a therapeutic agent that treats or prevents pain in a subject (e.g., a non-human mammal) are disclosed. The invention also features methods of treating or reducing pain in a subject (e.g., a human) by stimulating thalamic reticular nucleus (TRN) in the subject (e.g., a non-human mammal or a human), such as with electrical stimulation, optogenetic stimulation (e.g., using a laser-emitting optic fiber adapted for implantation in the brain of the subject), a therapeutic agent, thermal stimulation, or ultrasound stimulation. Accordingly, the invention can include a closed-loop system featuring, e.g., a therapeutic agent or neuromodulatory device.

A first aspect of the invention features a method for detecting pain in a subject (such as a mammal (e.g., a human)). The method includes (a) recording waveforms in brain tissue of the subject by EEG; (b) applying fast Fourier transfer (FFT) to convert the waveforms from the time domain to the frequency domain, thereby producing power spectral density (PSD); and (c) determining power amplitude from the PSD, in which an increase in the power amplitude from baseline serves as an indicator of pain. In some embodiments, the pain is selected from the group consisting of acute pain, inflammatory pain, and neuropathic pain. Preferably, the method further includes determining connectivity between brain regions, such as the coherence of brain regions from PSD, cross-frequency coupling, or Granger causality analyses.

For example, the method can further include the step of (d) determining coherence of brain regions from the FFT, in which an increase in the coherence of brain regions (e.g., the primary somatosensory cortex and prefrontal cortex) serves as an indicator of pain. In particular, the coherence of brain regions is determined from the difference in coherence at individual frequency units or frequency bands (e.g., about 3 Hz to about 30 Hz). For example, an increase in the coherence of brain regions indicates a transition from acute pain to chronic pain.

In some embodiments, the method can further include the step of administering a therapeutic agent to the subject (such as a mammal (e.g., a human)), e.g., to determine an effective amount of the therapeutic agent for the treatment or prevention of pain. In particular, there can be a decrease in the power amplitude after administering the therapeutic agent relative to baseline. Additionally, there can be a decrease in the coherence of brain regions after administering the therapeutic agent relative to baseline. The determining can also include repeating steps (a)-(d) of the method after administration of the therapeutic agent.

In some embodiments, the method can be performed on a second subject, e.g., in which the power amplitude from the PSD of the subject is compared to the second subject. Moreover, the method can be performed on the subject one or more times. The method can also be performed on a subject under anesthesia or during surgery.

The method of the first aspect can further include stimulating thalamic reticular nucleus (TRN) in the subject (e.g., a non-human mammal or a human), such as with electrical stimulation, optogenetic stimulation (e.g., using a laser-emitting optic fiber adapted for implantation in the brain of the subject), a therapeutic agent, thermal stimulation, or ultrasound stimulation. For example, a therapeutic agent can act on GABAergic neurons, such as therapeutic agents that target GABA receptors (e.g., barbiturates, bamaluzole, gabamide, y-Amino-o-hydroxybutyric acid (GABOB), gaboxadol, ibotenic acid, isoguvacine, isonipecotic acid, muscimol, phenibut, picamilon, progabide, quisqualamine, SL 75102, or thiomuscimol) or GABA transmitter uptake/trafficking (e.g., CI-966, deramciclane (EGIS-3886), gabaculine, guvacine (C10149), nipecotic acid, NNC 05-2090, NNC-711, SKF-89976A, SNAP-5114, tiagabine, or hyperforin).

In particular, there is a decrease in pain after stimulation of the TRN in the subject. The decrease in pain can be determined by repeating steps (a)-(c) of the method of the first aspect, e.g., in which a decrease in a theta frequency band from baseline indicates a reduction in pain of the subject. In particular, the TRN stimulation is at a frequency sufficient to treat or reduce pain, such as about 0.2 Hz to about 60 Hz (e.g., about 0.2 Hz, about 0.5 Hz, about 1 Hz, about 5 Hz, about 10 Hz, about 15 Hz, about 20 Hz, about 25 Hz, about 30 Hz, about 35 Hz, about 40 Hz, about 45 Hz, about 50 Hz, about 55 Hz, or about 60 Hz).

A second aspect of the invention features a method of treating or reducing pain in a subject (such as a mammal (e.g., a human)) by (a) recording waveforms in brain tissue of the subject by EEG; (b) applying FFT to convert the waveforms from the time domain to the frequency domain, thereby producing PSD; (c) determining power amplitude from the PSD; and (d) administering a therapeutic agent to the subject if there is an increase in the power amplitude from baseline. In some embodiments, the pain is selected from the group consisting of acute pain, inflammatory pain, and neuropathic pain. Preferably, the method further includes determining connectivity between brain regions, such as the coherence of brain regions from the FFT, cross-frequency coupling, or Granger causality analyses.

For example, the method can further include the step of (d) determining coherence of brain regions (e.g., the primary somatosensory cortex and prefrontal cortex) from the PSD, in which an increase in the coherence of the brain regions serves as an indicator of pain. In some embodiments, the coherence of brain regions is determined from the difference in coherence at individual frequency units or frequency bands (e.g., about 3 Hz to about 30 Hz). For example, an increase in the coherence of brain regions indicates a transition from acute pain to chronic pain.

The method can further include the step of determining an effective amount of the therapeutic agent for the treatment or prevention of pain in the subject (such as a mammal (e.g., a human)). For instance, if the therapeutic agent is effective, there can be a decrease in the power amplitude or coherence of brain regions after administering the therapeutic agent relative to baseline. The determining can further include repeating steps (a)-(d) of the method after administration of the therapeutic agent.

The method can also include administering one or more additional therapeutic agents to the subject. Furthermore, the determining can be performed, e.g., one or more times an hour, one or more times a day, or one or more times a month.

A third aspect of the invention features a method of screening for a therapeutic agent that treats or prevents pain in a subject (e.g., a non-human mammal). This method includes the steps of: (a) administering an agent to the subject that results in behavior associated with pain (e.g., hindpaw licking and flinching); (b) recording waveforms in brain tissue of the subject by EEG; (c) applying FFT to convert the waveforms from the time domain to the frequency domain, thereby producing PSD; (d) determining power amplitude from the PSD; (e) administering a test therapeutic agent to the subject; and (f) repeating steps (b)-(d), in which a decrease in the power amplitude relative to baseline indicates that the test therapeutic agent treats or prevents pain in the subject. In some embodiments, the pain is selected from the group consisting of acute pain, inflammatory pain, and neuropathic pain. Preferably, the method further includes determining connectivity between brain regions, such as the coherence of brain regions from FFT, cross-frequency coupling, or Granger causality analyses.

For example, the method can further include the step of determining coherence of brain regions (e.g., the primary somatosensory cortex and prefrontal cortex) from the PSD of the subject (e.g., a non-human mammal). In one embodiment, the coherence of brain regions (e.g., the primary somatosensory cortex and prefrontal cortex) is determined from the difference in coherence at individual frequency units or frequency bands (e.g., about 3 Hz to about 30 Hz). For example, a decrease in coherence of brain regions relative to baseline indicates that the test therapeutic agent treats or prevents pain in the subject (e.g., a non-human mammal).

A fourth aspect of the invention features a method of treating or reducing pain in a subject (e.g., a non-human mammal or a human) that includes stimulating TRN in the subject with electrical current or using a laser-emitting optic fiber adapted for implantation in the brain of the subject. The method can also include TRN stimulation using, e.g., a therapeutic agent, thermal stimulation, or ultrasound stimulation, to treat or reduce pain the subject. For example, a therapeutic agent can act on GABAergic neurons, such as therapeutic agents that target GABA receptors (e.g., barbiturates, bamaluzole, gabamide, y-Amino-o-hydroxybutyric acid (GABOB), gaboxadol, ibotenic acid, isoguvacine, isonipecotic acid, muscimol, phenibut, picamilon, progabide, quisqualamine, SL 75102, or thiomuscimol) or GABA transmitter uptake/trafficking (e.g., CI-966, deramciclane (EGIS-3886), gabaculine, guvacine (C10149), nipecotic acid, NNC 05-2090, NNC-711, SKF-89976A, SNAP-5114, tiagabine, or hyperforin).

The TRN stimulation is at a frequency sufficient to treat or reduce pain (e.g., acute pain, inflammatory pain, or neuropathic pain), such as about 0.2 Hz to about 60 Hz (e.g., about 0.2 Hz, about 0.5 Hz, about 1 Hz, about 5 Hz, about 10 Hz, about 15 Hz, about 20 Hz, about 25 Hz, about 30 Hz, about 35 Hz, about 40 Hz, about 45 Hz, about 50 Hz, about 55 Hz, or about 60 Hz). The method can further include determining a theta frequency band in brain tissue of the subject after the TRN stimulation, such that a decrease in the theta frequency band from baseline indicates a reduction in pain of the subject. For example, the method can further include: (a) recording waveforms in brain tissue of the subject by EEG; (b) applying fast FFT to convert the waveforms from the time domain to the frequency domain, thereby producing PSD; and (c) determining a theta frequency band from the PSD, such that a decrease in the theta frequency band from baseline indicates a reduction in pain of the subject.

In any of the above aspects, the waveforms can be recorded with one or more sensors (e.g., one or more electrodes) positioned on the skull of the subject. The waveforms can also be recorded with one or more sensors (e.g., one or more electrodes) attached to the scalp of the subject.

In any of the above aspects, the waveforms can be recorded at sample frequencies of about 2 Hz to about 35,000 Hz (e.g., sample frequencies of about 10 Hz to about 300 Hz). Additionally, brain activity can be recorded, e.g., by magnetoencephalography (MEG,) functional magnetic resonance imaging (fMRI), or positron emission tomography (PET).

Definitions

As used herein, "a" or "an" means "at least one" or "one or more" unless otherwise indicated. In addition, the singular forms "a," "an," and "the" include plural referents unless the context clearly dictates otherwise. Thus, for example, reference to a composition containing "a therapeutic agent" includes a mixture of two or more therapeutic agents.

As used herein, "about" refers to an amount±10 of the recited value.

As used herein, "acute pain" refers to a type of pain that typically lasts less than three to six months and/or pain that is directly related to soft tissue damage. Acute pain may follow non-neural tissue injury, for example, tissue damage from surgery or inflammation. Acute pain is of short duration and gradually resolves as the injured tissues heal.

As used herein, "chronic pain" refers to a type of pain that lasts longer than three to six months and/or pain that extends beyond the expected period of tissue healing. Chronic pain may originate with an initial trauma/injury or infection, or may be an ongoing cause of pain associated with neuropathic pain (e.g., diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathies, mono-neuropathies, or central pain syndrome), headaches, joint pain, backaches, sinus pain, muscle pain, nerve pain, and pain affecting specific parts of the body, such as shoulders, pelvis, and neck. Chronic pain may also be associated with lower back pain, arthritis, multiple sclerosis, fibromyalgia, shingles, nerve damage, or cancer.

As used herein, "coherence" refers to the magnitude squared coherence as a measure of power transfer between stochastic systems. The output of the function yields coherence values between 0 and 1, with a value of 1 signifying 100% perfectly matching amplitude difference between two waveforms at the observed frequency. For example, the coherence of brain regions is determined from the difference in coherence at individual frequency units or frequency bands (e.g., about 3 Hz to about 30 Hz).

As used interchangeably herein, the terms "decrease" and "reduce" refer to the ability to cause an overall decrease preferably of 20% or greater, more preferably of 50% or greater, and most preferably of 75%, 85%, 90%, 95%, or greater. Decrease or reduce may refer to, e.g., the symptoms of the disease, disorder, or pain in general or the determination of waveforms as recorded by the methods disclosed herein.

As used herein, the terms "electroencephalography" and "EEG" refer to an electrophysiological monitoring method to record electrical activity in brain tissue of a subject using one or more sensors attached to the scalp of a subject or with implantable sensors.

As used herein, "electrode" refers to an electric conductor through which an electric current enters or leaves an electrolytic cell or other medium. It further refers to the geometric configuration of discrete type electrical conductive elements capable of causing an electromagnetic field when a current and voltage is applied. The electrode can be of any shape, and can be symmetrically or asymmetrically configured. Size and shape depend on the specific requirements of the application.

As used herein, the phrase "fast Fourier transfer" or "FFT" is an algorithm used to convert waveforms from the time domain to the frequency domain. FFT may be implemented using a computing program including a computing language, e.g., MATLAB® (MathWorks), and/or a computing language, e.g., C, C++, Java, Fortran, or Python.

The abbreviation "fMRI," as used herein, refers to functional magnetic resonance imaging.

As used herein, the phrase "inflammatory pain" refers to a form of pain that is caused by tissue injury or inflammation (e.g., in postoperative pain or rheumatoid arthritis).

The abbreviation "MEG," as used herein, refers to magnetoencephalography.

As used herein, the term "naïve" refers to the state of a subject, such as a non-human mammal, prior to induction of a pain model, as described herein.

As used herein, the term "neuropathic pain" refers to pain caused by damage or disease affecting the somatosensory nervous system. For example, neuropathic pain includes, but is not limited to, diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathies, mono-neuropathies, or central pain syndrome, headaches, joint pain, backaches, sinus pain, muscle pain, nerve pain, and pain affecting specific parts of the body, such as shoulders, pelvis, and neck, and/or pain that is associated with lower back pain, arthritis, headache, multiple sclerosis, fibromyalgia, shingles, nerve damage, or cancer.

The abbreviation "PET," as used herein, refers to positron emission tomography.

As used herein, "power spectral density" or "PSD" refers to the numerical or visual representation (e.g., histogram) of the distribution of the power amplitude of a waveform as a function of frequency. Specific frequency bands may be evaluated using PSD, which include, but are not limited to, theta (e.g., 4-8 Hz), alpha (e.g., 8-12 Hz), beta (e.g., 12-25 Hz), and gamma (e.g., 25-100 Hz) frequency bands. Analysis of PSD outside of standard frequency bands (e.g. 6-15 Hz, 100-3000 Hz)) may also be evaluated using the methods described herein.

As used herein, "prevention" refers to a prophylactic treatment given to a subject who has or will have a disease, a disorder, a condition, or one or more symptoms associated with a disease, a disorder, or a condition.

As used herein, "therapeutic agent" refers to any agent that produces a healing, curative, stabilizing, or ameliorative effect. An "agent" may also be used, for example, to stimulate or cause a response in the subject, such as behavior in response to pain, e.g., hindpaw licking and flinching, in a non-human subject. In particular, a therapeutic agent may be included in a closed-loop system. For example, a therapeutic agent can act on GABAergic neurons to stimulate the thalamic reticular nucleus (TRN) in a subject, such as therapeutic agents that target GABA receptors (e.g., barbiturates, bamaluzole, gabamide, y-Amino-o-hydroxybutyric acid (GABOB), gaboxadol, ibotenic acid, isoguvacine, isonipecotic acid, muscimol, phenibut, picamilon, progabide, quisqualamine, SL 75102, or thiomuscimol) or GABA transmitter uptake/trafficking (e.g., CI-966, deramciclane (EGIS-3886), gabaculine, guvacine (C10149), nipecotic acid, NNC 05-2090, NNC-711, SKF-89976A, SNAP-5114, tiagabine, or hyperforin).

As used herein, "treating" refers to administering a pharmaceutical composition for prophylactic and/or therapeutic purposes. To "reduce the likelihood" refers to prophyactic treatment of a patient who is not yet ill, but who is susceptible to, or otherwise at risk of, a particular disease or condition (e.g., the conditions described herein, such as pain (e.g., acute pain, inflammatory pain, or neuropathic pain). To "treat disease" or use for "therapeutic treatment" refers to administering treatment to a patient already suffering from a disease to ameliorate the disease and improve the patient's condition. The term "treating" also includes treating a patient to delay progression of a disease or its symptoms. Beneficial or desired results can include, but are not limited to, alleviation, amelioration, or prevention of pain, a condition associated with pain, or one or more symptoms associated with pain.

As used interchangeably herein, the terms "subject" and "patient" refer to any animal (e.g., a mammal, e.g., a human). A subject to be treated or tested for responsiveness to a therapy according to the methods described herein can be one who has been diagnosed with pain.

As used herein, the phrase "waveform" refers to an extracellular local field potential measurement that represents the aggregate activity of a population of neurons. Measurements of waveforms may be used to determine neural activity in the central nervous system, e.g., the brain and spinal cord, or in peripheral nervous system.

The recitation herein of numerical ranges by endpoints is intended to include all numbers subsumed within that range (e.g., a recitation of 1 to 5 includes 1, 1.5, 2, 2.75, 3, 3.80, 4, and 5).

Other features and advantages of the invention will be apparent from the following Detailed Description and from the claims.

BRIEF DESCRIPTION OF THE DRAWINGS

FIGS. A-1C are an image and a series of graphs showing electrode placement and representative waveforms recorded using electroencephalography (EEG). Screw electrodes were placed stereotaxically over the primary somatosensory cortex (S1), specifically the ipsilateral S1(iS1) and contralateral S1 (cS1), and midline prefrontal cortex (PFC), according to Bregma coordinates (FIG. 1A). For a naïve rat, representative EEG cS1 waveforms down-sampled to 250 Hz and band-passed between 3-30 Hz, a spectrogram of the same EEG waveform, and the corresponding power spectral density (PSD) are shown (FIG. 1B). For a rat at day 7 (d7) after chronic constriction injury (CCI), representative EEG cS1 waveforms down-sampled to 250 Hz and band-passed between 3-30 Hz, a spectrogram of the same EEG waveform, and the corresponding PSD of are shown (FIG. 1C).

FIGS. 8A-8C are images of the study design (FIG. 8A) and corresponding waveforms (FIG. 8B) and source localization (FIG. 8C) of human subjects during a pain state, as detected using EEG.

FIG. 9C), and a representative coronal section showing electrolytic lesion (circle; arrows mark tetrode track) denoting a recording site in the ventral posterolateral (VPL) thalamus (white shadow in right panel; FIG. 9D).

FIG. 10A). SI power spectra are shown, in which the right panel inset shows a significant decrease in power within the theta band (3.8-8.5 Hz) following 10 Hz TRN stimulation in awake mice (n=5 mice; FIG. 10B). TRN stimulation increases burst firing in VPL neurons (n=17 units, 3-4 units per mouse; 5 mice) and increases the threshold of mechanical withdrawal to von Frey stimuli (d; n=4 mice; FIG. 10C-D).

FIG. 11A). Capsaicin increases burst firing in VPL neurons, which is further enhanced following TRN stimulation (n=17 units, 5 mice; FIG. 11B). Withdrawal thresholds following capsaicin indicate tactile allodynia, which is reversed upon TRN stimulation, but re-emerges 5 minutes afterwards (n=7 mice, FIG. 11C). A spectrogram illustrating the temporal dynamics of SI theta in relation to bursts in the VPL under naive, capsaicin, and capsaicin plus optogenetic conditions is shown (arrowhead marks light onset; gray line marks duration of optical stimulation; FIG. 11D). Note that theta and burst epochs do not temporally coincide. Dynamic, time-lagged cross-correlation between SI theta power relative to tonic and burst firing shows a significant negative correlation between theta-bursts when bursts precede theta by 120 ms (n=17 units; 5 mice; FIG. 11E).

DETAILED DESCRIPTION OF THE INVENTION

Figure 1A:
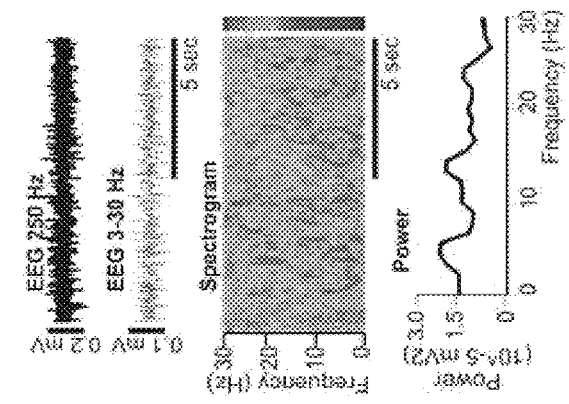

There is alack of reliable methods available for detecting and monitoring pain, particularly for determining effective therapeutic agents for a variety of conditions, disorders, and diseases associated with pain. I have developed a method of detecting pain in a subject (such as a mammal, e.g., a human) by recording waveforms in brain tissue using electroencephalography (EEG), applying fast Fourier transfer (FFT) to convert the waveforms from the time domain to the frequency domain, thereby producing power spectral density (PSD), and then determining power amplitude from the PSD. The methods disclosed herein can also be used, e.g., to treat or reduce pain in a subject, e.g., by administering a therapeutic agent to the subject, if there is an increase in the power amplitude from baseline. In particular, the methods are useful for detecting and treating or reducing acute pain, inflammatory pain, and neuropathic pain. Additionally, the methods can be used to screen for therapeutic agents that decrease power amplitude, and thus, treat or prevent pain in the subject. The invention also features methods to treat or reduce pain in a subject (such as a mammal, e.g., a human) by stimulating thalamic reticular nucleus (TRN) in the subject, such as with electrical stimulation, optogenetic stimulation (e.g., using a laser-emitting optic fiber adapted for implantation in the brain of the subject), a therapeutic agent, thermal stimulation, or ultrasound stimulation. Thus, the methods can feature a closed loop system including, e.g., a closed-loop system featuring, e.g., a therapeutic agent or neuromodulatory device.

Diagnostic Methods

Neuronal activity in a subject may be detected at the level of waveforms using EEG. In particular, analysis of waveforms in brain tissue using EEG allows for the study of multiple neuronal networks simultaneously. Waveforms may be recorded at sampling frequencies between about 2 Hz to about 35,000 Hz. Preferably, waveforms are recorded at sample frequencies between about 3 Hz to about 300 Hz. Waveforms may be recorded via EEG with one or more sensors (e.g., electrodes) positioned on the skull of the subject or with one or more sensors (e.g., electrodes) attached to the scalp of the subject. Other types of sensors include any sensor capable of detecting neuronal activity, e.g., calcium imaging, fMRI, MEG, MRI, and PET (acronyms defined below).

Neuronal waveforms may be detected by EEG with invasive methods (e.g., intraoperative or implantable sensors) or non-invasive methods (such as sensors, e.g., electrodes, attached to the scalp of a subject). These methods can include detecting shifts in PSD using FFT analysis to determine the occurrence or absence of new spectral peaks, shifts in peak amplitudes or peak latency from a PSD. Methods of detecting waveforms in brain tissue of a subject may further include the use of magnetoencephalography (MEG) in addition to other types of imaging techniques and brain scans (for example, magnetic resonance imaging (MRI), functional magnetic resonance imaging (fMRI), and positron emission tomography (PET)) in combination with EEG. Such techniques may be applied to a subject prior to, concurrently, or subsequent to recording of waveforms using EEG.

Thus, the present invention provides methods for detecting waveforms in brain tissue of a subject (e.g., a mammal, e.g., a human) indicative of pain using EEG. These methods feature the detection of waveforms in brain tissue of a subject, e.g., as a biomarker for pain, such as acute pain, inflammatory pain, and neuropathic pain. The neuronal activity patterns that make up the pain biomarker can be divided into two major categories: spontaneous (e.g., independent or temporally not associated with an overt stimulus or identifiable cause) and evoked (e.g., activity correlated with an overt stimulus or identifiable cause). Both forms of pain may be detected using these methods.

The methods can also be performed one or more (e.g., two, there, four, or five) times to detect waveforms in brain tissue of a subject (e.g., a mammal, e.g., a human) indicative of pain using EEG at intervals (e.g., in seconds, minutes, or in hours), irregularly, or continuously. In particular, the methods using EEG are performed in intervals of seconds, such as for 1, 2, 3, 4, 5, 6, 7, 8, 9, 10, 11, 12, 13, 14, 15, 20, 25, 30, 35, 40, 45, 50, 55, or 60 seconds, to detect waveforms in brain tissue indicative of pain.

Pain

Pain is associated with a wide range of medical conditions. The present invention features methods for diagnosing and treating a subject (e.g., a mammal, such as a human) with pain or conditions associated with pain. The methods of diagnosis and treatment are based, inter alia, on the inventor's discovery that waveforms in brain tissue of a subject detected by EEG are indicative of pain. Subjects diagnosed and treated using the methods can include subjects with acute pain, subacute pain, or chronic pain (e.g., pain that lasts longer than three to six months or pain that extends beyond the expected period of healing); or conditions associated with pain (e.g., post-herpetic neuralgia, trigeminal neuralgia, phantom limb pain, carpal tunnel syndrome, sciatica, pudendal neuralgia, complex regional pain syndrome, or central pain syndrome, headaches, in particular, migraine, joint pain, backaches, sinus pain, muscle pain, nerve pain, and pain affecting specific parts of the body, such as shoulders, pelvis, and neck, and/or pain that is associated with lower back pain, arthritis, headache, fibromyalgia, shingles, or nerve damage).

Methods described herein may be useful for the diagnosis, treatment, reduction, or prevention of various forms of pain, whether acute or chronic. Exemplary conditions that may be associated with pain include, for example, soft tissue, joint, and bone inflammation and/or damage (e.g., acute trauma, osteoarthritis, or rheumatoid arthritis), myofascial pain syndromes (fibromyalgia), headaches (including cluster headache, migraine, and tension type headache), myocardial infarction, angina, ischemic cardiovascular disease, post-stroke pain, sickle cell anemia, peripheral vascular occlusive disease, cancer, inflammatory conditions of the skin or joints, diabetic neuropathy, and acute tissue damage from surgery or traumatic injury (e.g., burns, lacerations, or fractures).

For example, the present invention provides methods for detecting and treating inflammatory pain. Inflammatory pain is a form of pain caused by tissue injury or inflammation (e.g., in postoperative pain or rheumatoid arthritis). Following a peripheral nerve injury, symptoms are typically experienced in a chronic fashion, distal to the site of injury and are characterized by hyperesthesia (enhanced sensitivity to a natural stimulus), hyperalgesia (abnormal sensitivity to a noxious stimulus), allodynia (widespread tenderness associated with hypersensitivity to normally innocuous tactile stimuli), and/or spontaneous burning or shooting lancinating pain. In inflammatory pain, symptoms are apparent, at least initially, at the site of injury or inflamed tissues and typically accompany arthritis-associated pain, musculo-skeletal pain, and postoperative pain. The different types of pain may coexist or pain may be transformed from inflammatory to neuropathic during the natural course of the disease, as in post-herpetic neuralgia.

Additionally, the present invention provides methods for detecting and treating neuropathic pain. Neuropathic pain can take a variety of forms depending on its origin and can be characterized as acute, subacute, or chronic depending on the duration. Acute pain can last anywhere from a couple hours to less than 30 days. Subacute pain can last from one to six months and chronic pain is characterized as pain that lasts longer than three to six months or pain that extend beyond the expected period of healing. In neuropathic pain, the pain may be described as being peripheral neuropathic if the initiating injury occurs as a result of a complete or partial transection of a nerve or trauma to a nerve plexus. Peripheral neuropathy can result from traumatic injuries, infections, metabolic disorders, diabetes, and/or exposure to toxins. Alternatively, neuropathic pain is described as being central neuropathic following a lesion to the central nervous system, such as a spinal cord injury or a cerebrovascular accident. The methods of the invention include administration of the compositions described herein to treat neuropathic pain. Types of neuropathic pain include but are not limited to: diabetic peripheral neuropathy, post-herpetic neuralgia, trigeminal neuralgia, phantom limb pain, carpal tunnel syndrome, sciatica, pudendal neuralgia, complex regional pain syndrome, sensory polyneuropathies, mono-neuropathies, and central pain syndrome.

The present invention may also be useful for the diagnosis, treatment, reduction, or prevention of musculo-skeletal pain (after trauma, infections, and exercise), pain caused by spinal cord injury, tumors, compression, inflammation, dental pain, episiotomy pain, deep and visceral pain (e.g., heart pain, bladder pain, or pelvic organ pain), muscle pain, eye pain, orofacial pain (e.g., odontalgia, trigeminal neuralgia, glossopharyngeal neuralgia), abdominal pain, gynecological pain (e.g., dysmenorrhea and labor pain), pain associated with nerve and root damage due to trauma, compression, inflammation, toxic chemicals, hereditary conditions, central nervous system pain, such as pain due to spinal cord or brain stem damage, cerebrovascular accidents, tumors, infections, demyelinating diseases including multiple sclerosis, low back pain, sciatica, and post-operative pain.

Methods of Treatment

The present invention provides methods of treating or reducing pain in a subject (e.g., a mammal, such as a human) by recording waveforms in brain tissue of the subject using EGG, applying FFT to convert waveforms from the time domain to the frequency domain, thereby producing PSD, determining power amplitude from the PSD, and administering a therapeutic agent to the subject, if there is an increase in the power amplitude from baseline. Additionally, waveforms recorded in brain tissue of a subject by EEG can be used to determine coherence of brain regions, in which an increase in the coherence of brain regions (e.g., the PFC and S1) is indicative of, e.g., a transition from acute pain to chronic pain. Accordingly, a therapeutic agent can be administered after determining an increase in brain region coherence. Thus, the methods result in a reduction in the likelihood of pain or prevention of pain.

The methods of the present invention for treating or reducing pain in a subject may be performed on the subject within 24 hours (e.g., within 20 hours, 16 hours, 12 hours, 8 hours, 4 hours, 3 hours, 2 hours, or 1 hour) of an initial presentation of the subject to a medical professional. The method may also be performed at least 24 hours (e.g., at least 48 hours, 3 days, 4 days, 5 days, 6 days, or one week) after an initial presentation of the subject to a medical professional. The method may be performed on a subject previously admitted to a medical facility for a disease or disorder. The method may also be performed one or more (e.g., two, there, four, or five) times for treating a subject at intervals (e.g., hourly, daily, weekly, or monthly) or irregularly.

Upon assessing that there is an increase in the power amplitude from baseline, a therapeutic agent may be administered to the subject one or multiple times daily (e.g., two times, three times, up to four times a day), weekly (or at some other multiple day interval), or on an intermittent schedule, with that cycle repeated a given number of times (e.g., 2, 3, 4, 5, 6, 7, 8, 9, or 10 cycles) or indefinitely. According to the methods described herein, therapeutic agents may also be administered chronically (e.g., more than 20 days, e.g., 21 days, 30 days, 60 days, 3 months, 6 months, 9 months, 1 year, 2 years, or 3 years). Sensors of the present method may also be coupled to an 'effector' (e.g. pharmacotherapy or neuromodulatory device) in an automated closed-loop system.

The present invention also provides methods of treating or reducing pain (e.g., acute pain, inflammatory pain, or neuropathic pain) in a subject (e.g., a mammal, such as a human) by stimulating thalamic reticular nucleus (TRN) in the subject. In particular, methods of treating or reducing pain in a subject feature stimulation of TRN using, e.g., electrical stimulation, optogenetic stimulation (e.g., using a laser-emitting optic fiber adapted for implantation in the brain of the subject), a therapeutic agent, thermal stimulation, or ultrasound stimulation. For example, the TRN can be stimulated at a frequency of about 0.2 Hz to about 100 Hz, such as about 0.2 Hz, about 0.5 Hz, about 1 Hz, about 5 Hz, about 10 Hz, about 15 Hz, about 20 Hz, about 25 Hz, about 30 Hz, about 35 Hz, about 40 Hz, about 45 Hz, about 50 Hz, about 55 Hz, about 60 Hz, about 65 Hz, about 70 Hz, about 75 Hz, about 80 Hz, about 85 Hz, about 90 Hz, about 95 Hz, or about 100 Hz. In particular, TRN stimulation can be intermittent or 'burst' stimulation, such as about 100 Hz to about 200 Hz bursts of individual stimulation epochs. Additionally, the TRN of the subject can be stimulated with a laser-emitting optic fiber one or multiple times daily (e.g., two times, three times, up to four times a day), weekly (or at some other multiple day interval), or on an intermittent schedule, with that cycle repeated a given number of times (e.g., 2, 3, 4, 5, 6, 7, 8, 9, or 10 cycles), or indefinitely. For example, a therapeutic agent may also be administered to the subject to stimulate the TRN in the subject, thereby treating or reducing pain in the subject. In particular, a therapeutic agent can target GABA receptors (e.g., barbiturates, bamaluzole, gabamide, y-Amino-o-hydroxybutyric acid (GABOB), gaboxadol, ibotenic acid, isoguvacine, isonipecotic acid, muscimol, phenibut, picamilon, progabide, quisqualamine, SL 75102, or thiomuscimol) or GABA transmitter uptake/trafficking (e.g., CI-966, deramciclane (EGIS-3886), gabaculine, guvacine (C10149), nipecotic acid, NNC 05-2090, NNC-711, SKF-89976A, SNAP-5114, tiagabine, or hyperforin).

The methods of the present invention for treating or reducing pain in a subject (e.g., a mammal, such as a human) featuring TRN stimulation may be performed on the subject within 24 hours (e.g., within 20 hours, 16 hours, 12 hours, 8 hours, 4 hours, 3 hours, 2 hours, or 1 hour) of an initial presentation of the subject to a medical professional. The method of TRN stimulation may also be performed at least 24 hours (e.g., at least 48 hours, 3 days, 4 days, 5 days, 6 days, or one week) after an initial presentation of the subject to a medical professional. The method of TRN stimulation may be performed on a subject previously admitted to a medical facility for a disease or disorder associated with pain (e.g., acute pain, inflammatory pain, or neuropathic pain). The method of TRN stimulation may also be performed one or more (e.g., two, there, four, or five) times for treating a subject at intervals (e.g., hourly, daily, weekly, or monthly) or irregularly. Additionally, TRN stimulation may be performed on a subject having pain as determined by, e.g., recording waveforms in brain tissue of the subject by EEG; applying FFT to convert the waveforms from the time domain to the frequency domain, thereby producing PSD; and determining power amplitude from the PSD, in which an increase in the power amplitude from baseline serves as an indicator of pain. The subject may also have not previously received treatment for pain prior to the methods.

Dosing of Therapeutic Agents

Methods of the present invention may be used to determine the effective amount of the therapeutic agent (e.g., dosage or titration) to treat or prevent the likelihood of pain in a subject (such as a mammal, e.g., a human). In particular, an effective amount of the therapeutic agent results in, e.g., an amelioration or stabilization of pain in the subject, such that there is a decrease in the power amplitude of the PSD relative to baseline.

The recording, applying, and determining steps of the method may be repeated after administration of the therapeutic agent in order to determine an effective amount of the agent. These steps may be repeated one or more times an hour (e.g., within 1 minute, 5 minutes, 10 minutes, 15 minutes, 30 minutes, 45 minutes), day (e.g., within 12 hours, 8 hours, 4, hours, 2 hours, 1 hour), or month (e.g., at least 48 hours, 3 days, 4 days, 5 days, 6 days, or one week). Suitable therapeutic agents also include combinations thereof, such that one or more (e.g., two, three, four, or five or more) additional therapeutic agents is administered to the subject. When co-administered, the two therapeutic agents are desirably administered within 24 hours of each other (e.g., within 12 hours, 8 hours, 4, hours, 2 hours, 1 hour, 30 minutes, 15 minutes, or substantially simultaneously).

Actual dosage levels of the active ingredients in the therapeutic agents administered according to the present invention may be varied so as to obtain an amount of the active ingredient which is effective to achieve the desired response of treating or reducing the likelihood of pain in a subject, without undesirable side effects or being toxic to the subject (such as a mammal, e.g., a human). According to the methods of the present invention, the selected dosage level can be determined by recording waveforms in brain tissue of the subject by EEG. For instance, after administering an agent to the subject that results in behavior associated with pain, assessment of a decrease in the power amplitude relative to baseline indicates that the test therapeutic agent treats or prevents pain in the subject and can be used to select the appropriate dosage of the test therapeutic agent. Additionally, side effects associated with analgesics (e.g., drowsiness with gabapentanoids or an increase in coherence values with mexiletine) can be determined with the methods.

The selected dosage level will also depend upon a variety of pharmacokinetic factors including the activity of the therapeutic agents, the route of administration, the time of administration, the rate of absorption of the particular agent being employed, the duration of the treatment, other drugs, substances, and/or materials used in combination with the particular compositions employed, the age, sex, weight, condition, general health and prior medical history of the subject being treated, and like factors well known in the medical arts. It is to be understood that, for any particular subject, specific dosage regimes should be adjusted over time according to the individual need and the professional judgment of the person administering or supervising the administration of the compound. For example, the dosage of a therapeutic agent can be increased if the lower dose does not provide sufficient activity to decrease power amplitude relative to baseline as assessed by the methods described herein. Conversely, the dosage of a therapeutic agent may be maintained or decreased if there is an appreciable decrease in power amplitude relative to baseline.

Therapeutic agents can include, pharmacological, non-pharmacological, and neuromodulatory agents (e.g. deep brain stimulation, spinal cord stimulation, transcranial current stimulation, transcranial magnetic stimulation, and ultrasound stimulation). In particular, therapeutic agents useful in the methods include non-steroidal anti-inflammatory drug (NSAIDs). Exemplary NSAIDs include, without limitation, ibuprofen, aceclofenac, acemetacin, acetaminophen, aloxiprin, aspirin, benorilate, bromfenac, celecoxib, deracoxib, diclofenac, diflunisal, ethenzamide, etodolac, etofenamate, etoricoxib, fenbufen, fenoprofen, flufenamic acid, flurbiprofen, lonazolac, lornoxicam, indomethacin, isoxicam, kebuzone, ketoprofen, ketorolac, licofelone, loxoprofen, lumiracoxib, meclofenamic acid, mefenamic acid, meloxicam, metamizol, mofebutazone, naproxen, nabumetone, niflumic acid, nimesulide, oxaprozin, oxyphenbutazone, parecoxib, phenidone, phenylbutazone, piroxicam, propacetamol, propyphenazone, rofecoxib, salicyamide, sulfinpyrazone, sulindac, suprofen, tiaprofenic acid, tenoxicam, or tolmetin. Therapeutic agents useful in the methods can also include anticonvulsants, such as pregabalin, carbamazepine, flupirtine, gabapentin, lamotrigine, oxcarbazepine, phenytoin, retigabine, topiramate, or valproate. Additionally, useful therapeutic agents of the methods include antiarrhythmic agents, such as mexiletine, lidocaine, or tocainide.

Methods of Screening Therapeutic Agents

The present invention features methods of screening for a therapeutic agent using a non-human animal subject (e.g., mammal) that include administering an agent to the subject that results in behavior associated with pain (e.g., hindpaw licking and flinching); recording waveforms in brain tissue of the subject by EEG, applying FFT to convert the waveforms from the time domain to the frequency domain, thereby producing PSD; determining power amplitude from the PSD; administering a test therapeutic agent to the subject; and repeating the prior recording, applying, and determining steps. In particular, a decrease in the power amplitude relative to baseline indicates that the test therapeutic agent treats or prevents pain in the subject.

Test therapeutic agents of the present invention may be screened from a plurality of chemical entities. The steps of screening for a therapeutic agent may be repeated with one or more compounds, e.g., with a library of compounds. For instance, the invention may feature a library comprising compounds or complexes that may treat or reduce the likelihood of pain the subject. Screening of multiple compounds can be carried out simultaneously or concurrently; or can be carried out simultaneously with some compounds and then concurrently with others. Therapeutic agents may include pharmacological, non-pharmacological, and neuromodulatory agents, as described herein.

Clinical Applications

In addition to using the methods of the present invention for detecting pain in a subject (such as a mammal, e.g., a human) and/or treating or reducing the likelihood of pain, the present methods may be used during invasive or surgical procedures (e.g., intraoperative, awake light sedation, or unconscious deep anesthesia), in particular if anesthetics or sedatives are contraindicated. Furthermore, the diagnostic methods of the present invention are useful for subjects or patients that are non-cooperative, in a non-communicating vegetative state, cognitively impaired, facing language barrier, or where verbal reporting is unreliable (e.g., in pediatric neonate subjects).

Methods of the present invention also provide for safe, effective, and long-term treatment strategies for pain using, e.g., a neuromodulatory system for the relief of chronic pain. The methods may also include providing therapeutic neurostimulation to the brain of the patient, e.g., at predefined times, frequencies, voltages, periodicities, and currents. For instance, these methods can involve electrodes implanted into a subjects brain, e.g., a deep brain stimulation system, electrodes on the scalp, e.g., a transcranial direct current stimulation system, and/or the use of magnetic stimulation, e.g., a transcranial magnetic stimulation system. The neurostimulation can be provided in response to detecting an increase in EEG power amplitude indicative of pain or on a periodic basis (e.g., every 1-2 hours). Methods of the present invention can also include the use of a transdermal patch placed on the skin for drug delivery or an intrathecal drug delivery pump for direct delivery of medication.

The following examples are intended to illustrate, rather than limit, the disclosure. These studies feature the use of EEG recording methods in awake, freely-behaving rats to demonstrate that pain modulates neuronal oscillations in clinically relevant models and that effective analgesic drugs reverse this modulation. These results suggest that recording waveforms in brain tissue of subjects using EEG can be used to predict spontaneous nociceptive states in rodents and that waveforms associated with pain can be used for diagnostic and therapeutic purposes.

Example 1. Electrophysiological Measurements Using Clinically Tethered Electrodes Experiments were performed on male Sprague-Dawley rats (n=43 rats, weight of 200 to 300 g). Animals were housed under a 12-hour light/dark cycle in a temperature- and humidity-controlled environment. Under deep anesthesia (isoflurane, 3.5%), the head was fixed in a stereotaxic apparatus. A small skin incision was used to expose the skull. Two stainless steel screw electrodes (0-80 ga, ⅛-inch, and impedance of 0.6 Ohm; Component Supply Company, Fort Meade, Fla.) were placed over the intact skull corresponding to the primary somatosensory cortex (S1) hindlimb area bilaterally without craniotomy (Bregma −2, 2 mm lateral) and a third screw was placed over the area corresponding to the prefrontal cortex (PFC; Bregma +3.5 mm, midline). Minimal craniotomies were used to place three stabilization screws (corresponding to Bregma +1.4, 2 mm bilaterally and Bregma −4.8 mm, midline) to anchor all EEG electrodes chronically using dental acrylic. EEG screws were threaded with a silver wire and attached to a female miniature pin connector (A&M Systems, Sequim, Wash.). Signal reference was provided by a silver wire permanently threaded to skin at the back of the neck.

EEG recordings began five to seven days after implantation of contralateral S1 (cS1), ipsilateral S1(iS1), and PFC electrodes, as described above (FIG. 1A). EEG waveforms were amplified (DAM80, World Precision Instruments, Sarasota, Fla.), led to a processing system (micro1401mkII, Cambridge Electronic Design (CED), Cambridge, UK), and analyzed off-line using Spike 2 (CED) or MATLAB® (Mathworks, R2012b, Natick, Mass.). Prior to EEG recording, pin connectors from each electrode were tethered to pre-amplifier headstages leading to a multichannel amplifier (iso-DAMA, WPI Inc., Sarasota, Fla.). Amplification for each channel was set at ×1000. This system allowed free movement of tethered rats with no head restraint, while recording EEG signals simultaneously from all electrodes (cS1, iS1, and PFC). Rats were allowed to freely navigate individually in Plexiglas chambers. The rat's behavior was visually monitored, noting periods of rest. Each EEG recording session was approximately five minutes per animal, irrespective of the pain model. Of that 5 minute interval, 15 second segments were selected randomly during the rest state with one 15 second segment selected per condition and per animal. After 15 minutes of acclimation, EEG waveforms were sampled at 25 kHz and down-sampled offline to 250 Hz.

Only data during awake, resting periods (defined as alertness with no locomotor behavior) were further analyzed. Potentials generated due to vigorous myogenic activity, such as scratching, were excluded from analysis. These artifacts were identified by monitoring the animal's behavior, voltage amplitude, and spectral frequency (e.g., greater than 30 Hz). Study exclusion criteria included signs of skin infection due to surgical complications from the EEG implant or low signal-to-noise ratio indicating faulty electrophysiological signal transmission. No rat was excluded from the capsaicin or Complete Freund's Adjuvant (CFA) groups. Three rats were excluded from the chronic constriction injury (CCI) treatment group due to high noise in the electrophysiological signal at a later stage of CCI.

Example 2. Pain Models, Thermal Sensitivity, and Analgesic Treatment

Seven days after implantation of EEG electrodes, different pain models were induced. For capsaicin as a model of acute pain, capsaicin (0.1%, 40 µL, Sigma-Aldrich) was intradermally injected in the left hindpaw under brief isoflurane anesthesia (1.5% for 2 minutes). A transient receptor potential vanilloid 1 agonist, capsaicin increases neuronal firing in nociceptors, mainly polymodal C-fibers, and is commonly used as a model of acute nociceptive pain. Within 24 hours after capsaicin injection, nocifensive behavior indicative of spontaneous pain, such as hindpaw licking and flinching, completely subsides. Sham capsaicin rats received only vehicle injections (20 µL, 7% Tween 80 in saline).

For Complete Freund's Adjuvant (CFA) as a model of inflammatory pain, CFA (100 µL, intradermal, Sigma-Aldrich) was injected in the left hindpaw under brief isoflurane anesthesia (1.5% for 2 minutes). CFA-induced nociceptive behaviors result from the edema caused by the inflammatory response to heat-killed Mycobacterium tuberculosis in the inoculate and persists for more than 2 days after injection. Sham CFA rats received vehicle injections (100 µL, incomplete Freund's adjuvant as 85% paraffin oil and 15% mannide monooleate).

For chronic constriction injury (CCI) as a model of neuropathic pain, the left sciatic nerve was exposed unilaterally after skin incision at the mid-thigh level and blunt dissection of the biceps under deep anesthesia (isoflurane, 3.5%). Four chromic gut (4-0) ligatures were tied loosely around the nerve 1 mm apart, and the overlying muscles and skin were closed in layers with 4-0 Ethilon™ sutures. A minor modification was introduced, consisting of loose ligatures, to minimize nerve damage and deafferentation. Rats with this slightly modified CCI procedure gradually develop typical signs of sensory hypersensitivity associated with neuropathic pain, such as guarding the affected hindpaw and thermal hypersensitivity, for more than 2 weeks after CCI. Sham CCI animals underwent the same procedures without nerve ligation.

Thermal sensitivity of the hindpaw was assessed by measuring the latency of the withdrawal reflex in response to a radiant heat source. Individual animals were placed in a Plexiglas box on an elevated glass plate under which a radiant heat source (4.7 amps) was applied to the plantar surface of the hindpaw after 15 minutes of acclimation. Paw withdrawal latencies (PWL) in response to four thermal stimulations, separated by five minutes of rest, were averaged for each paw. Rats unresponsive to radiant heat stimuli were excluded from PWL data analysis.

For analgesic treatment, ibuprofen was dissolved in a 5% solution of 2-hydroxypropy-p-cyclodextrin (Sigma-Aldrich) formulated to deliver 30 mg/kg in a volume of 3 m/kg. Pregabalin was dissolved in 5% Tween 80 (Sigma-Aldrich) in saline. Mexiletine was dissolved in saline for intraperitoneal (i.p) delivery of 10 mg/kg in a volume of 3 m/kg. EEG was performed 30 min after i.p. delivery of analgesics. Ibuprofen was administered concomitantly with capsaicin to allow at least 30 minutes for the analgesic effects to manifest. Pregabalin was administered at day 2 (d2) after CFA treatment and day 14 (d14) after CCI treatment. Mexiletine was administered at day 16 (d16) after CCI treatment in the same rats that received pregabalin to allow within group comparison of analgesic effects.

Example 3. Analysis of EEG Waveform Recordings

Fast Fourier transform (FFT) was used to convert EEG waveforms from the time domain to the frequency domain, yielding power spectra. Power values were generated in 27 frequency bins between 3 and 30 Hz. For each experimental condition, 15 second continuous segments during complete rest were selected for power analysis.

The magnitude squared coherence function (mscohere) in MATLAB® Signal Processing Toolbox or the "COHER" script in Spike 2 was used as a measure of power transfer between stochastic systems. The output of the function yields coherence values between 0 and 1, with a value of 1 signifying perfectly matching amplitude difference between two waveforms at the observed frequency. For signals x and y, the magnitude squared coherence is a function of their power spectral densities $P_{xx}(f)$ and $P_{yy}(f)$ and their cross power spectral density $P_{xy}(f)$:

$$C_{xy}(f) = |P_{xy}(f)|^2 / P_{xx}(f) P_{yy}(f)$$

The function parameters were defined as follows: the fast Fourier transfer length ("nfft") is the next power of 2 greater than the length of each signal, the sampling frequency ("fs") is 250, the window length ("window") is the periodic Hamming window to obtain 8 equal sections of each signal, and the number of overlapping samples ("noverlap") is the value yielding 50% overlap. To minimize type I errors, coherence values were down-sampled from 54 to 27 frequency bins between 3 and 30 Hz. Two-way ANOVA analysis followed by Bonferroni's correction was used to compute statistical significance. Bartlett's test was performed to compute normal distribution and equal variance. A 'p' value <0.05 was considered significant (denoted with * in figures). All values are reported as ±standard error of the mean.

Example 4. EEG Power, Pain, and Nociceptive Behavior

Figure 1B:
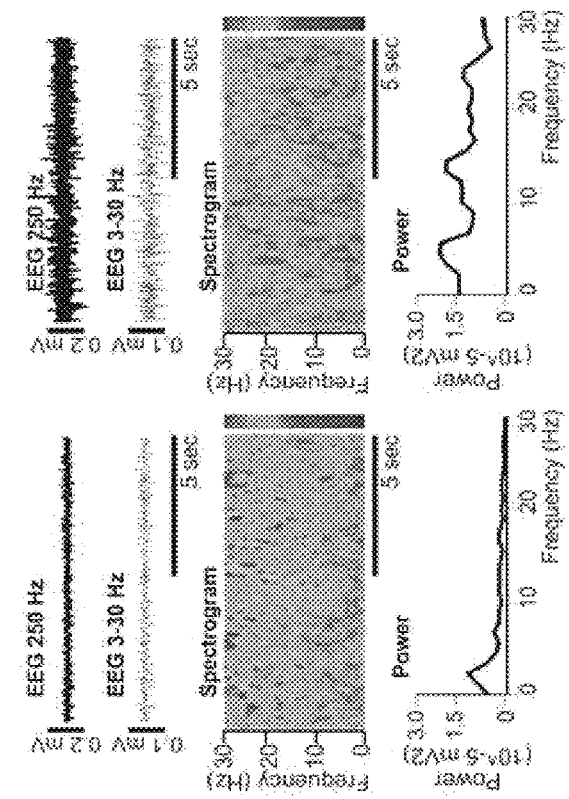
Figure 1C:
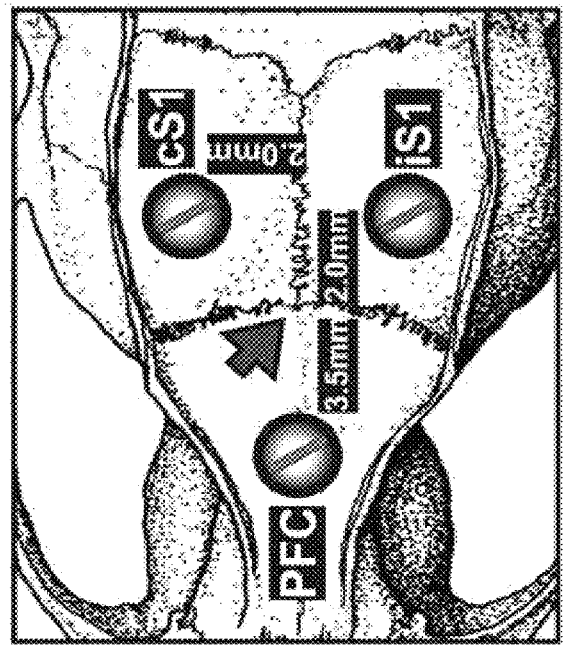
Figure 2A:
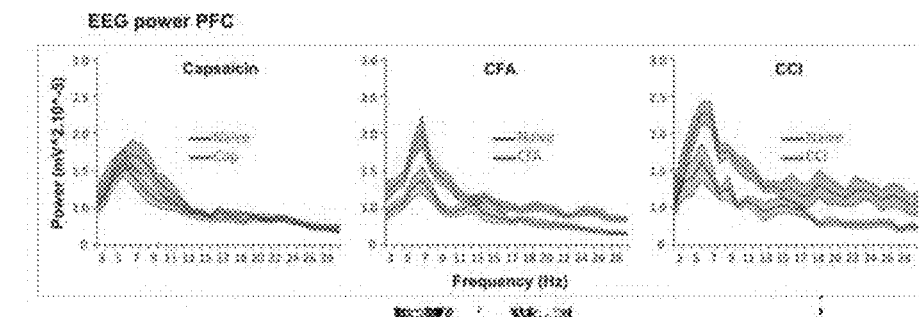
FIGS. 2A-2C are a series of graphs showing EEG power spectra recorded for PFC (FIG. 2A), cS1 (FIG. 2B), and iS1 (FIG. 2C) at 30 minutes after capsaicin, day 2 (d2) after Complete Freund's Adjuvant (CFA), and d7 after CCI (shaded areas represent standard error of the mean).
Figure 2A:
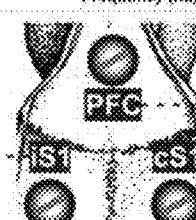
Figure 2B:
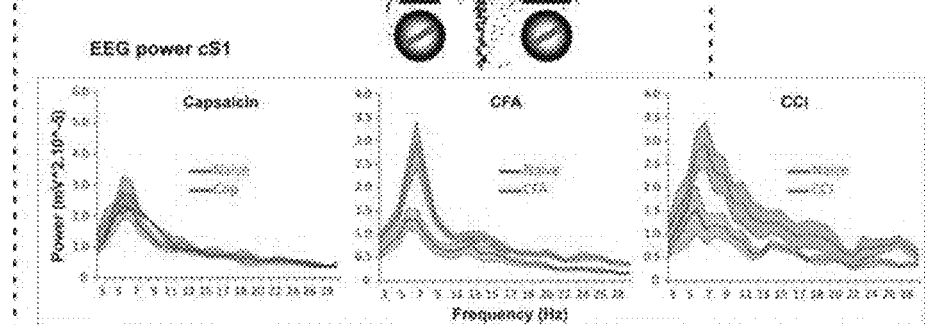
Figure 2C:
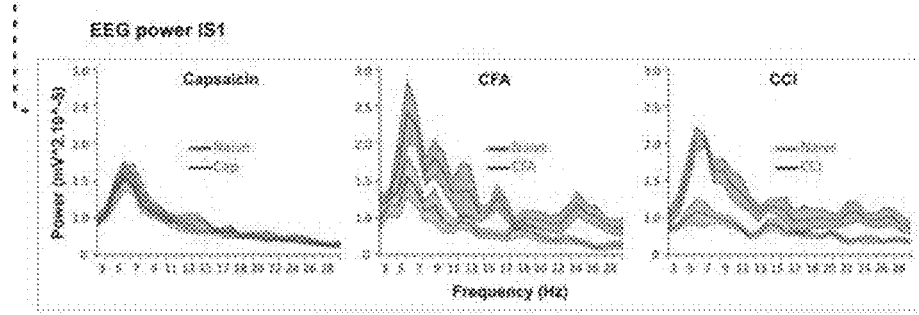

EEG recordings were performed in awake, freely-behaving rats during rest. EEG waveforms were generally stable over time, allowing for a reliable analysis of longitudinal EEG data. When 10 second interval EEG waveforms (sampling frequency of 250 Hz) were band-pass filtered between 3-30 Hz, increased voltage amplitude and oscillations were evident in corresponding spectrograms and power spectra of the cS1 of a rat at seven days following CC1 relative to a naïve rat (FIG. 1B-1C). In particular, the spectrogram of the naïve versus the CC1 treated rat revealed increased low-frequency power (<10 Hz) in the cS1 at seven days following CC1.

EEG power waveforms from iS1, cS1, and PFC relevant to acute (capsaicin, n=8 rats), inflammatory (d2 after CFA, n=10 rats for PFC and cS1, n=4 rats for iS1), and neuropathic pain states (d14 after CCI, n=5 rats for PFC and cS1, n=6 rats for iS1) are shown in FIG. 2. Compared to naïve rats, EEG power amplitude in the 3-30 Hz range of the iS1, cS1, or PFC was more synchronized following CFA or CCI (FIG. 2A-2C). There was no remarkable difference of EEG power spectra between iS1, cS1, or PFC, suggesting that pain is associated with widespread synchronization of EEG. Interestingly, capsaicin, which evokes a transient and relatively less pronounced state of nociception within 30 minutes after intradermal injection, resulted in a modest increase in EEG power amplitude compared to CFA and CCI, which arguably evoke a more heightened nociceptive state. EEG power amplitude increased in the three pain models, except for power recorded over iS1, which remained unchanged in rats with capsaicin.

Figure 3A:
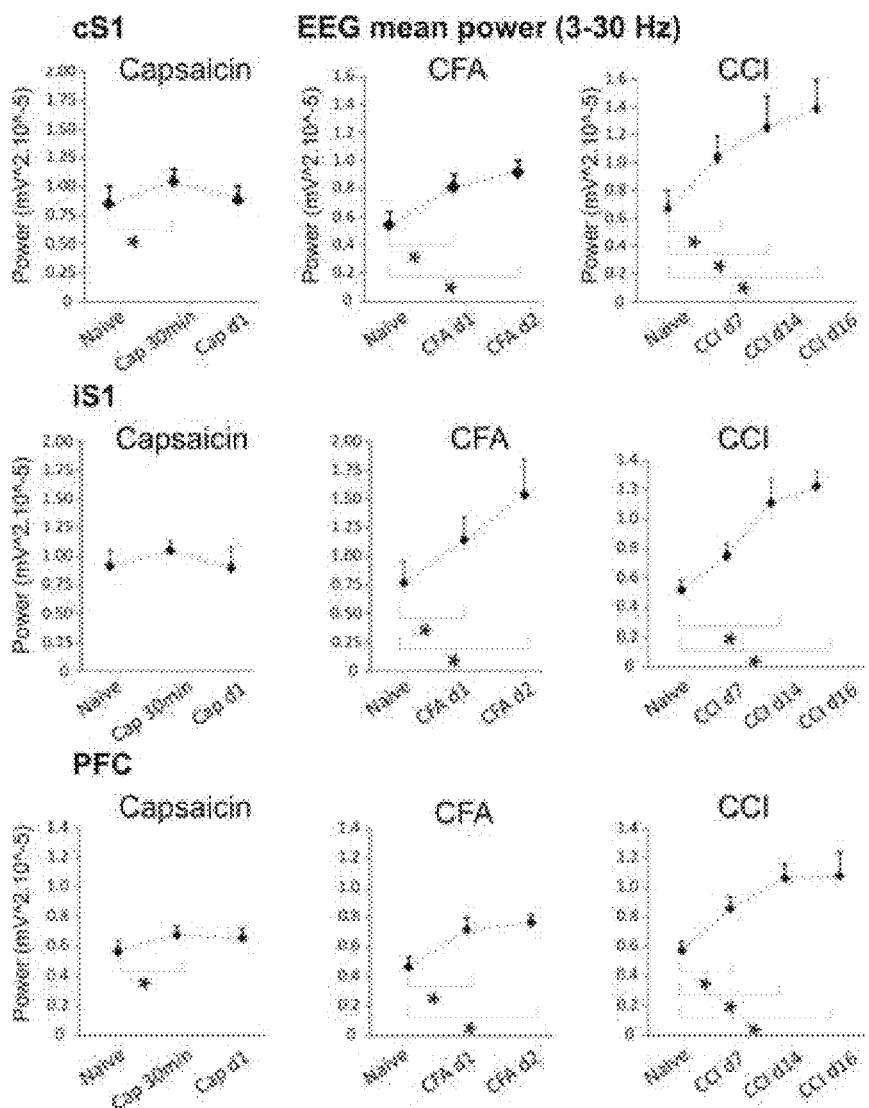
FIGS. 3A-3B are a series of graphs showing EEG mean power amplitude over time after capsaicin, CFA, or CCI (FIG. 3A) and thermal hyperalgesia, as determined by paw withdrawal latency (PWL), after capsaicin, CFA, or CCI (FIG. 3B).

Mean EEG power ($mV^2 \times 10^{-5}$) between 3 Hz to 30 Hz of the cS1, iS1, and PFC followed an ascending, linear trend during the development of inflammatory pain due to CFA and neuropathic pain due to CCI (FIG. 3A). For cS1, EEG mean power was not changed 30 min after capsaicin (1.05±0.11, n=8 rats) compared to naïve rats (from 0.85±0.15) or 24 hours after capsaicin (0.89±0.12). In contrast, CFA increased EEG mean power from 0.54±0.10 (naïve) to 0.81±0.10 and 0.91±0.09 within one and two days, respectively (p<0.05, n=10 rats). CCI increased EEG mean power from 0.67±0.13 (naïve) to 1.03±0.15, 1.25±0.23, and 1.39±0.21 at 7, 14, and 16 days after injury, respectively (p<0.05, n=5 rats).

For iS1, mean power increased from 0.91±0.13 (naïve) to 1.05±0.8 at 30 min after capsaicin (p<0.05), and reversed 24 hours after capsaicin to naïve levels (0.90±0.18; n=8 rats). CFA increased mean power from 0.76±0.19 (naïve) to 1.13±0.20 and 1.53±0.03 within one and two days, respectively (p<0.05, n=4 rats). CCI increased mean power from 0.52±0.07 (naïve) to 0.75±0.08, 1.11±0.16, and 1.22±0.10 at 7, 14, and 16 days after injury, respectively (p<0.05, n=6 rats).

For PFC, mean EEG power increased from 0.56±0.08 (naïve) to 0.67±0.06 at 30 min after capsaicin (p<0.05), and reversed 24 hours after capsaicin to naïve levels (0.65±0.07; n=8 rats). CFA increased mean power from 0.46±0.07 (naïve) to 0.72±0.08 and 0.76±0.06 within one and two days, respectively (p<0.05, n=10 rats). CCI increased mean power from 0.58±0.06 (naïve) to 0.86±0.08, 1.06±0.10 and 1.08±0.16 at 7, 14, and 16 days after injury, respectively (p<0.05, n=5 rats).

In summary, nociceptive states in rat models of acute, inflammatory, and neuropathic forms of pain were discovered to correlate with increased EEG power over cS1 and PFC. Notably, EEG power in S1 ipsilateral after capsaicin injection was not significantly changed. These data further suggest that power spectra in iS1 to noxious stimuli might encode long-lasting, but not transient forms of pain, indicating that S1 is critical for sensory discrimination and localization of acute, noxious stimuli on the contralateral side of the body. Notably, intradermal capsaicin injection elicits pain that has maximal intensity immediately upon injection with rapid decay within 5 minutes. Secondary hyperalgesia occurs at a later time point starting at 10 minutes after injection and persists at least 20 minutes thereafter. In the present study, capsaicin was injected under brief (2-3 minute) isoflurane sedation and collection of EEG data began 30 minutes after injection. Accordingly, the present EEG data correspond to a time point of secondary, not primary, hyperalgesia. Thus, long-term pain leads to widespread increases in EEG power according to an anatomical representation that does not strictly overlap with the cortical projection map of the spinothalamic system.

Example 5. Relationship of EEG Power and Thermal Hyperalgesia

Figure 3B:
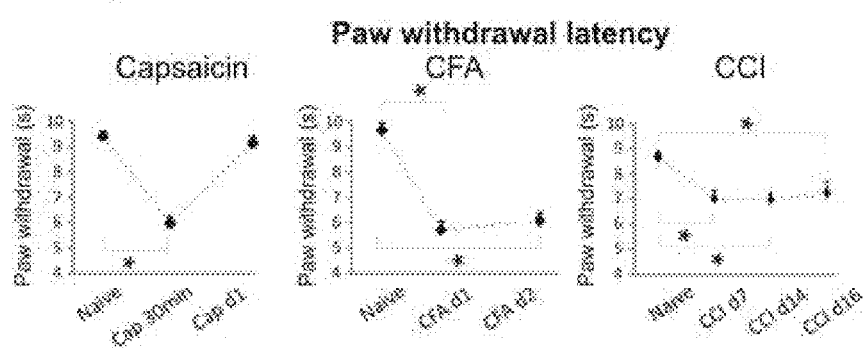

The relationship between EEG power and thermal hyperalgesia, a widely-used correlate of pain-induced behavioral hypersensitivity, was then determined. Thermal hyperalgesia developed reliably in all pain models as determined from paw withdrawal latencies (PWL; FIG. 3B). PWL decreased from 9.43±0.22 seconds to 6.00±0.24 seconds at 30 min after capsaicin (p<0.05), and reversed to 9.15±0.26 seconds at 24 hour after capsaicin (n=8 rats). CFA decreased PWL from 9.67±0.29 seconds (naïve) to 5.73±0.36 seconds and 6.10±0.33 seconds within one and two days, respectively (p<0.05, n=10 rats). CCI decreased PWL from 8.71±0.21 seconds (naïve) to 7.03±0.36, 7.00±0.24, and 7.26±0.45 seconds at 7, 14, and 16 days after injury, respectively (p<0.05, n=7 rats). Notably, the modulation of mean power versus PWL was not identical. For example, in rats with CCI, near-perfect linear trends in mean power were observed for iS1, PFC and cS1 ($R^2$=0.96, 0.89, and 0.95, respectively), whereas a near-perfect polynomial trend was observed for PWL at the same longitudinal time points.

The present EEG data reflect a spontaneous, 15 second interval during resting state, whereas the behavioral data represent an evoked, paw withdrawal reflex. Generally, an increase in EEG power correlated with a decrease in the latency of PWL. This relationship was consistent for capsaicin and CFA conditions across waveforms recorded via all three EEG electrodes, with the exception of iS1 after capsaicin, as discussed above. Moreover, a longitudinal inverse plateau trend was observed in PWL, whereby values at d7, d14, and d16 after CCI were not statistically different, in contrast to the ascending linear trend over time for S1 EEG mean power. Thus, EEG power provides valuable information regarding the chronic nociceptive state, which cannot be inferred from solely PWL.

Example 6. Effect of Administering Analgesics on EEG Power

The sensitivity of EEG power to analgesic treatment was investigated using the clinically relevant drugs ibuprofen, pregabalin and mexiletine. Ibuprofen, a NSAID cyclooxygenase inhibitor, is widely used as a non-prescription analgesic which was initially developed for mild forms of musculoskeletal and arthritis pain. Pregabalin, an anticonvulsant α2δ-subunit ligand, is clinically effective for the management of peripheral neuropathic pain and post-incisional pain, as well as cutaneous and muscle hyperalgesia in inflammatory models of muscle pain. Mexiletine, a nonselective, use-dependent voltage-gated sodium channel blocker (which is also anti-arrhythmic), has been shown to suppress persistent sodium currents in peripheral sensory axons of patients and is considered a third-line treatment for neuropathic pain.

Figure 4A:
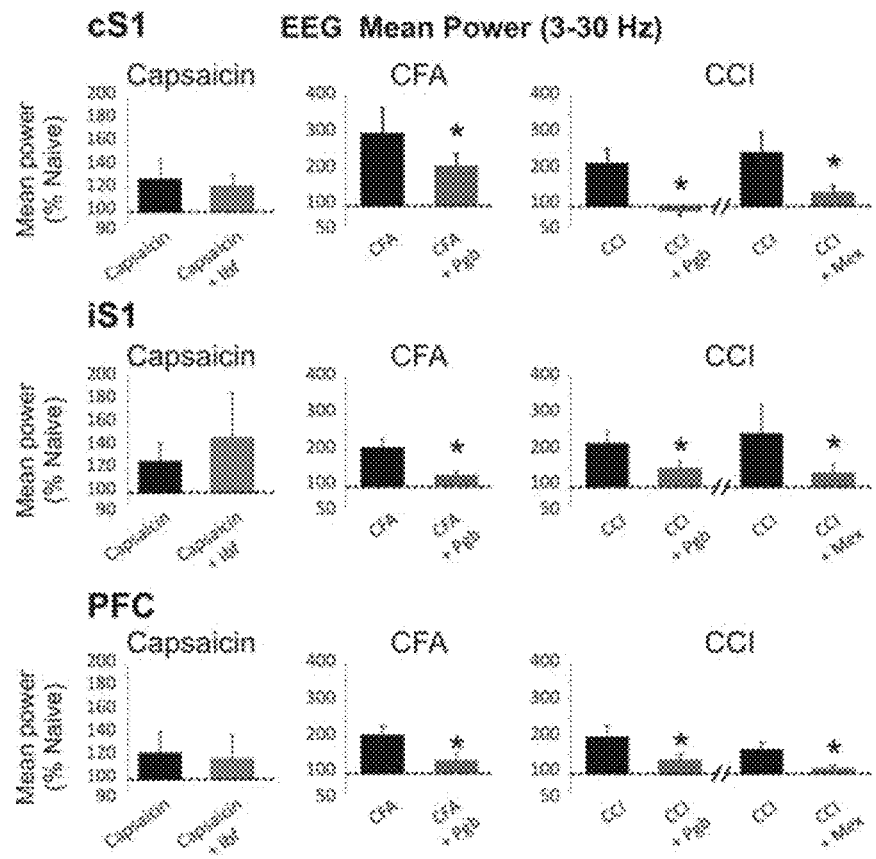
FIGS. 4A-4B are a series of graphs showing EEG mean power amplitude over time after capsaicin, CFA, or CCI and capsaicin, CFA, or CCI followed by treatment with ibuprofen, pregabalin, or mexiletine (FIG. 4A). Thermal hyperalgesia for each pain model followed by treatment with ibuprofen, pregabalin, or mexiletine was also determined using PWL (FIG. 4B).

For cS1, treatment with ibuprofen (FIG. 4A) did not have a significant effect on EEG mean power (122±10, n=4 rats) compared to capsaicin alone (128±17; n=8 rats), whereas pregabalin treatment in rats with CFA reduced mean power from 299±70 to 209±35 (p<0.05, n=7 rats; FIG. 4A). In rats with CCI, treatment with pregabalin or mexiletine reduced mean power from 217±39 to 87±12 (p<0.05, n=5 rats) and from 245±56 to 134±18 (p<0.05, n=5 rats), respectively. Similar results were observed for PFC and iS1.

For PFC, treatment with ibuprofen did not have a significant effect on EEG mean power (117±18, n=4 rats) compared to capsaicin alone (123±16; n=8 rats), whereas pregabalin treatment in rats with CFA reduced mean power from 208±26 to 138±20 (p<0.05, n=5 rats). In rats with CCI, treatment with pregabalin or mexiletine reduced EEG mean power from 188±27 to 133±14 (p<0.05, n=7 rats), and from 156±10 to 113±6 (p<0.05, n=6 rats), respectively. For iS1, treatment with ibuprofen did not have a significant effect on mean power (143±35, n=4 rats) compared to capsaicin alone (124±14; n=8 rats), whereas pregabalin treatment in rats with CFA reduced EEG mean power from 20824 to 133±9 (p<0.05, n=5 rats). In rats with CCI, treatment with pregabalin or mexiletine reduced EEG mean power from 219±32 to 151±20 (p<0.05, n=6 rats), and from 247±78 to 13926 (p<0.05, n=8 rats), respectively.

Figure 4B:
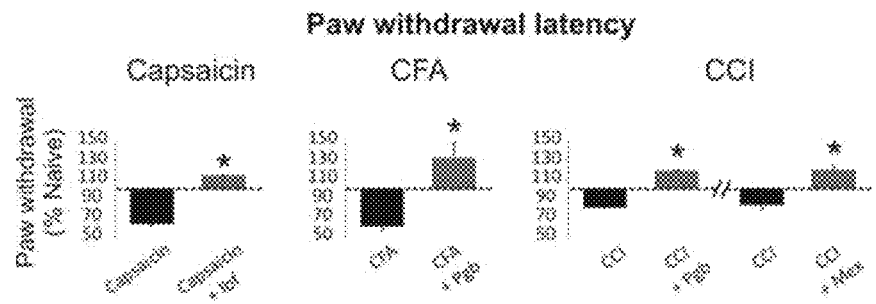

The analgesic effect of these drugs was also tested behaviorally in the same animals. Although ibuprofen had no effect on EEG mean power following capsaicin, ibuprofen blocked thermal hyperalgesia by increasing PWL from 64±3 (n=8 rats) to 114±10 (p<0.05, n=4 rats; FIG. 4B). Pregabalin also increased PWL in rats with CFA from 60±3 to 132±17 (p<0.05, n=5 rats). In rats with CCI, treatment with pregabalin or mexiletine increased PWL from 81±3 to 119±5 (p<0.05, n=7 rats) and from 83±5 to 119±17 (p<0.05, n=7 rats), respectively.

In summary, ibuprofen was effective in attenuating thermal hyperalgesia, but did not have a significant effect on EEG power, which could result from the differential effects of the mechanism of action of ibuprofen on evoked versus spontaneous pain. Otherwise, pregabalin and mexiletine effectively blocked thermal hyperalgesia and reversed EEG mean power to normal levels in rats with CFA and CCI. These results further confirm that pregabalin and mexiletine, at the optimal analgesic doses used in this study, did not manifest adverse EEG signs, such as diffuse or paroxysmal slow activity that is often associated with drowsiness and would have an enhancing effect on EEG power in the low-frequency range.

Example 7. Coherence of Brain Regions Following Pain

Figure 5A:
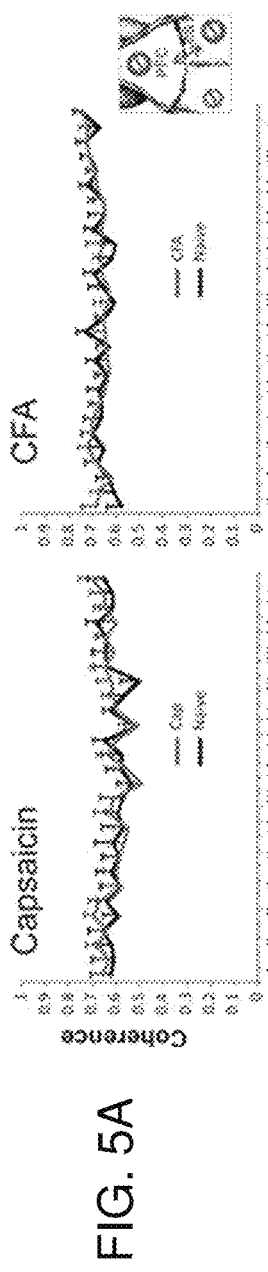
FIGS. 5A-5C are graphs showing cortical coherence between PFC and cS1 (FIG. 5A), iS1 and PFC (FIG. 5B), and iS1 and cS1 (FIG. 5C) after capsaicin, CFA, or CCI and capsaicin, CFA, or CCI followed by treatment with ibuprofen, pregabalin, or mexiletine.

The effect of pain on cortico-cortical S1-PFC coherence was also investigated. Coherence in the 3-30 Hz range between cS1-PFC increased in rats more than 14 days after CCI, whereas capsaicin and CFA did not cause a significant change in cS1-PFC coherence (FIG. 5A). In particular, coherence between cS1 and PFC (following values are mean 3-30 Hz coherence) did not change in rats with capsaicin (0.60±0.06 in naïve and 0.61±0.05 in capsaicin; n=7 rats) or CFA (0.67±0.4 in naïve and 0.67±0.03 in CFA; n=11 rats). Similarly, cS1-PFC coherence was not changed in rats at day 7 (d7) after CCI (0.68±0.05) compared to naïve (0.65±0.04; n=5 rats), whereas it was significantly (p<0.05) increased starting at day 14 (d14) following nerve injury (0.71±0.04; n=5 rats). Analgesic treatment with pregabalin or mexiletine reversed cS1-PFC coherence (p<0.05), with mexiletine having a more pronounced attenuating effect (0.71±0.04 for CCI d14 and 0.61±0.03 after pregabalin and 0.68±0.03 for CCI d16 and 0.50±0.10 after mexiletine, respectively; n=5 rats). Similarly, capsaicin and CFA did not significantly effect cS1-iS1 coherence and iS1-PFC coherence.

Figure 5B:
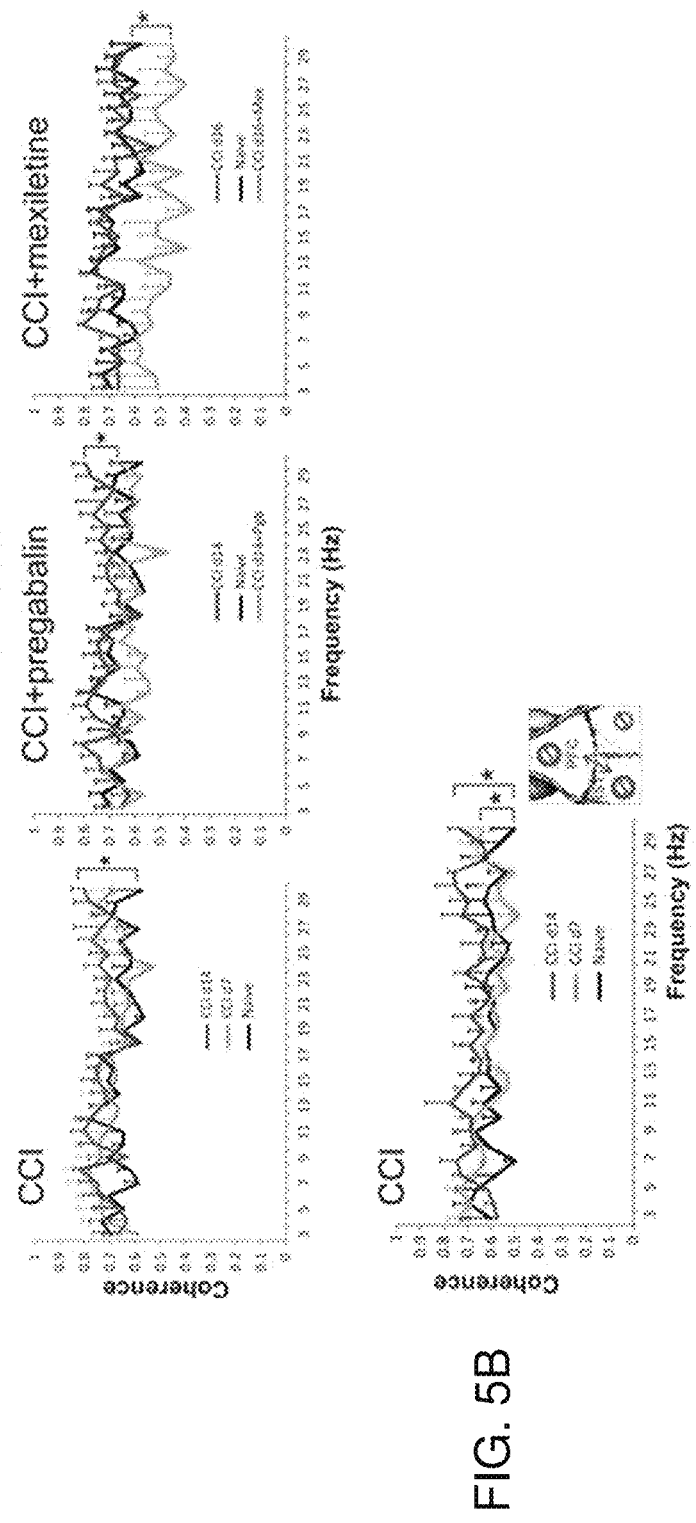
Figure 5C:
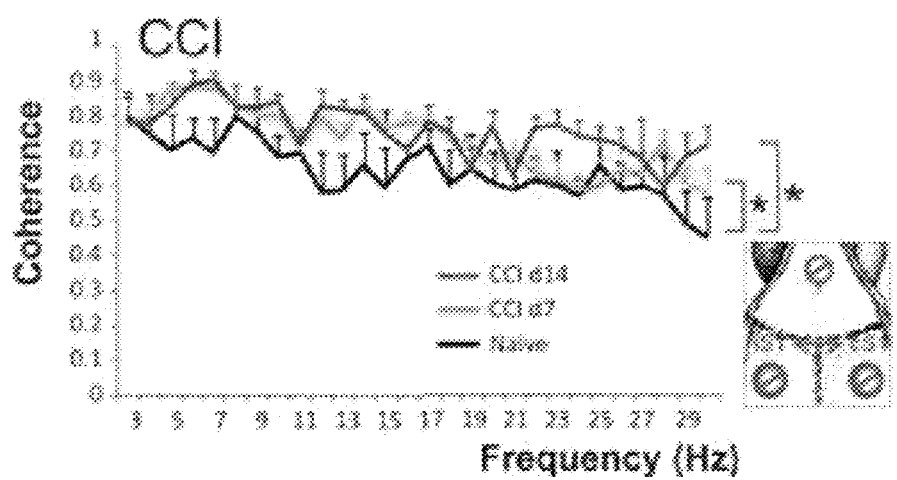

Coherence between iS1 and PFC was significantly (p<0.05) enhanced at d7 (0.61±0.03; n=6 rats) and d14 (0.69±0.04 compared to naïve 0.59±0.06) after CCI (FIG. 5B.) Coherence between cS1 and iS1 was also significantly (p<0.05) enhanced at d7 (0.63±0.06 in naïve compared to 0.72±0.02 d7; n=6 rats) and d14 (0.63±0.06 in naïve compared to 0.75±0.04 d14; n=6 rats) after CCI (FIG. 5C).

In summary, S1-PFC coherence is enhanced in rats at d14 after CCI, corresponding to a late-stage neuropathic pain. This result indicates that increased functional connectivity between S1-PFC may predict pain transition from an acute to a chronic stage. In contrast, inter-hemispheric coherence between iS1 and cS1 increases in rats with CCI as early as d7 after CCI.

Figure 6:
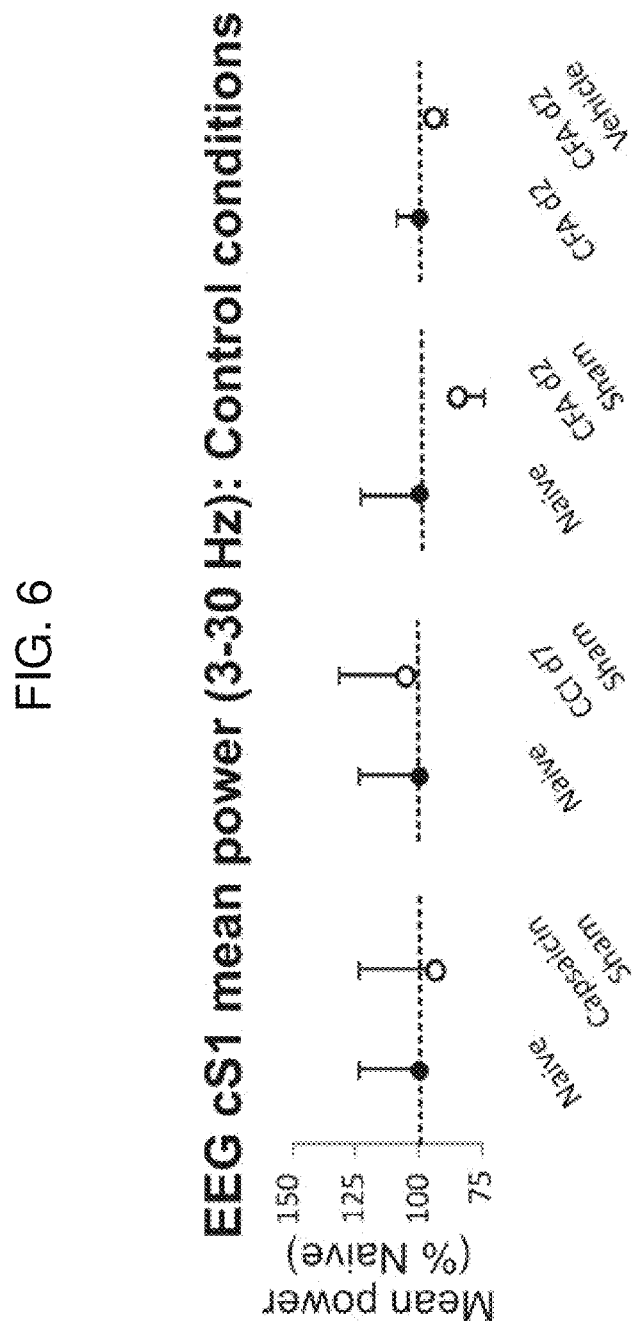
FIG. 6 is a graph showing control conditions using sham pain models and vehicle drug treatments.

Lastly, control experiments demonstrated that cS1 mean EEG power did not significantly changed in rats following capsaicin sham (93±31 versus 100±24 in naïve; n=3 rats), d7 CCI sham (105±27 versus 100±24 in naïve; n=6 rats), and d2 CFA sham (85±11 versus 100±23 in naïve; n=5 rats; FIG. 6). We also confirmed that intradermal vehicle injection in the left hindpaw of rats at d2 after CFA had no effect on mean cS1 EEG power (94±4 compared to CFA d2 pre-vehicle 100±9; n=4 rats). Moreover, coherence in the 3-30 Hz range between waveforms recorded via pairs of EEG electrodes did not change in these same control experiments.

Figure 12:
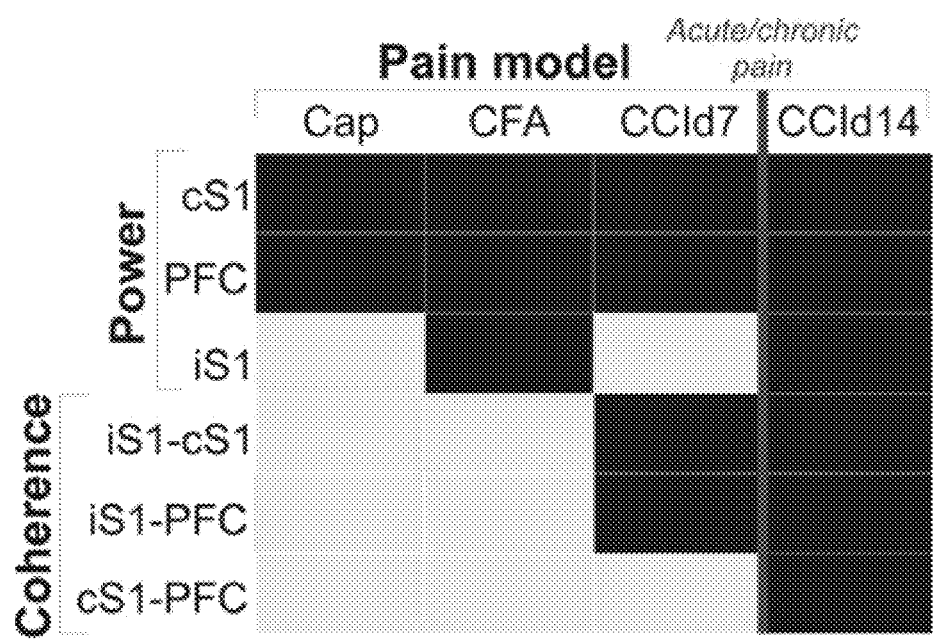
FIG. 12 is a graph showing a summary of EEG results in different pain models. Black cells represent significant increases compared to naïve rats.

In the present study, we used a relatively non-invasive EEG recording methods in awake, freely behaving rats to demonstrate that pain modulates on-going oscillations in clinically relevant models and that effective analgesic drugs reverse this modulation. These results suggest that brain oscillations predict spontaneous nociceptive states in rodents (FIG. 12).

Example 8. Increased PSD During Pain States in Humans

Figure 7:
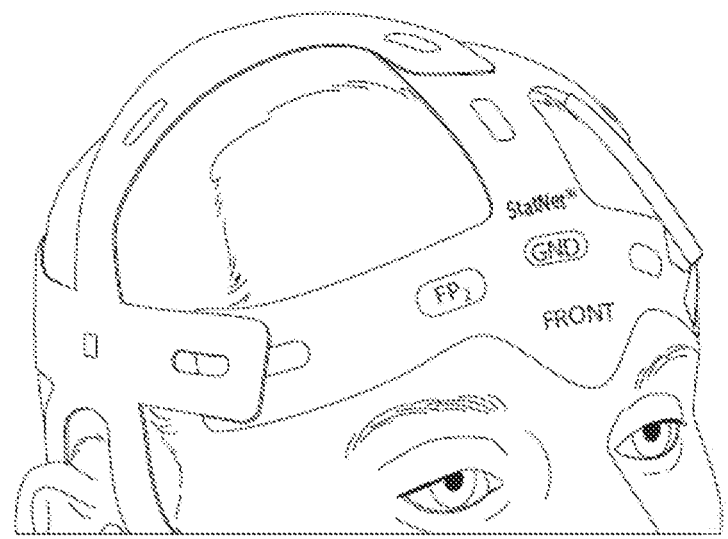
FIG. 7 is an image of a wireless, 16-electrode, single-use EEG system used to study waveforms in human subjects after pain.

A wireless, 16-electrode, single-use EEG system (Stat-Net™; BioSignal) was used to determine waveforms in brain tissue of healthy human subjects during a pain state of distress-tolerance (FIG. 7). Subjects were randomized to receive ice water or room temperature water for 20 second intervals. Subjects submerged a hand in the bucket of water (ice water or room temperature) and were then asked to rate their pain score at various times (FIG. 8A). Subjects who received ice water reported a lower pain score during the first 10 seconds of submersion compared to the last 10 seconds of submersion. There was an increase in power in the theta range (6-7 Hz) associated with the higher pain score at the Fz placement electrode (FIG. 8B). Source localization showed a prominent 6-7 Hz increase in power corresponding to Fz, which overlaps with frontal cortex in humans and PFC in rats (FIG. 8C). Subjects who received room temperature water did not exhibit an increase in power corresponding to the Fz and did exhibit decreased PSD across multiple frequency bands (3-30 Hz) in caudal brain regions.

Example 9. Determination of Theta Oscillations in Somatosensory Cortex and Thalamic Bursts Following Pain Experiments were performed to investigate the relationship between pain behavior, theta (4-8 Hz) oscillations in somatosensory cortex, and burst firing in thalamic neurons in vivo. Thalamic bursts are triggered predominantly by GABAergic drive from the reticular thalamic nucleus (TRN), a thin layer overlaying the thalamus that receives strong input from limbic cortical areas. To selectively induce thalamic bursts, TRNs were optically stimulated in awake, unrestrained transgenic mice co-expressing the vesicular GABA transporter (VGAT) with Channelrhodopsin-2 (ChR2). In these mice, ChR2 expression in the thalamus is restricted to the TRN. Age-matched wild-type (C57 Bl\6J) non-ChR2 expressing mice were also used to control for non-specific optical stimulation effects. The naïve state refers to normal conditions prior to induction of the pain models.

Figure 9A:
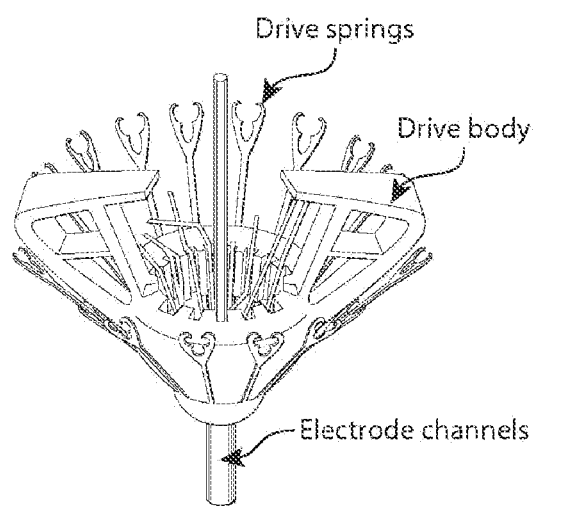
FIGS. 9A-9D are images of extracellular in vivo recording. Shown are the assembly of the FlexDrive stereotrode system mounted with a fiberoptic ferrule (FIG. 9A), isolation of two putative single-units from a 300-3000 Hz band-pass local field potential (FIG. 9B), channelrhodopsin-2 expression restricted to thalamic reticular nucleus (TRN) in a transgenic mouse co-expressing the vesicular GABA transporter (VGAT.
Figure 9A:
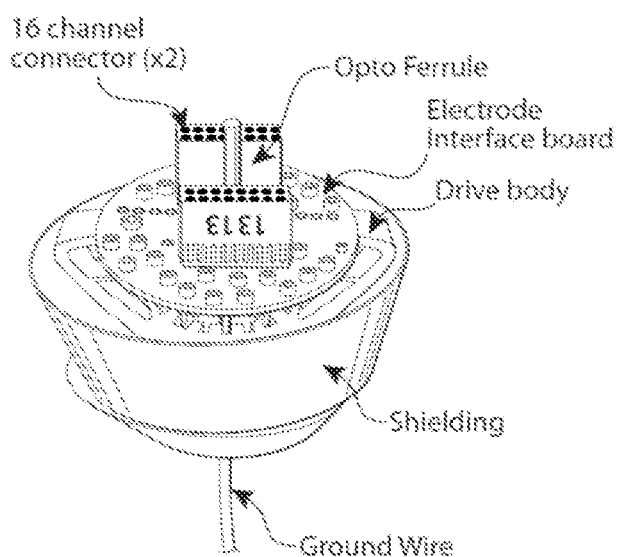
Figure 9B:
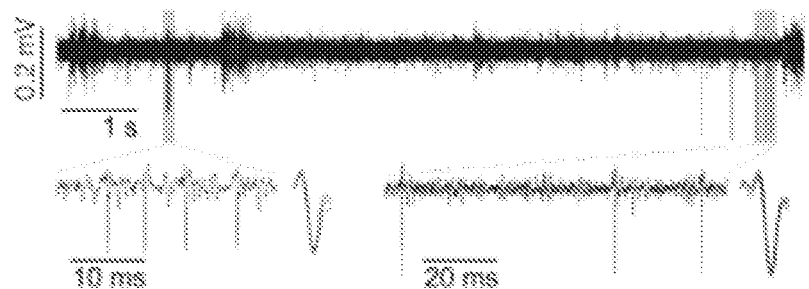

A custom-made multi-channel system was used to record extracellularly from putative single-units in ventral postero-lateral (VPL) thalamus and local field potential (LFP) in the primary somatosensory cortex (S1) hindlimb area (FIGS. 9A-9B). For a description of the FlexDrive system assembly see www.open-ephys.org/flexdrive. Drives were positioned over the right side of the brain targeting the VPL thalamus (Bregma −1.22 to −1.40, 1.75 to 2.00 lateral, 3 to 4 mm vertical) and SI cortex (Bregma −0.86 to −1.10, 1.5 to 1.8 lateral, <0.5 mm vertical). In each mouse, 3-4 tetrodes were positioned in VPL or SI and one tetrode in TRN, where an optical fiber was positioned over the somatosensory TRN (Bregma −1.20 to −1.34, 2.30 to 2.40 lateral, 3.5 mm vertical). FlexDrives were fixed to the skull using C&B-METABOND® Quick! Adhesive (Parkell). After 3 days postoperatively, tetrodes were lowered incrementally (~500 µm over 5-7 days) until auditory confirmation of typical neuronal responses as expected in VPL and SI (e.g., increased multiunit firing) evoked by light brushing of the left hindpaw. Tetrode positions were also corroborated by stereotaxic coordinates. Additional criteria for identifying VPL units included peak-to-trough duration of the action potential and the observations that most VPL neurons increase in firing rate in response to gentle brushing and noxious pinch of the receptive field (i.e. wide dynamic range type) while TRN neurons are predominantly inhibited. Chronic implants were stable over several weeks, allowing longitudinal analysis of neuronal activity with behavioral testing of mechanical sensitivity.

For electrophysiological recording in naturally behaving mice, mice were briefly sedated (1% isoflurane <2 min) to allow connection of the FlexDrive to two-16 channels preamplifier (TDT RA16PA), headstages (TDT LP16CH) and a fiber optic patch cord (200 µm). Unrestrained mice later recovered from sedation in a 3×3" PLEXIGLAS® enclosure for at least 15 minutes prior to the start of electrophysiological recording using a TDT RZ2 BioAmp processor at 24.4 kHz sampling rate per channel. Two sequential notch filters (58-62 Hz) were applied to reduce electrical interference. The behavior of the animal was noted to determine alert rest periods, defined as alertness with no vigorous movements such as grooming or scratching. At the end of the final recording session, electrolytic lesions were performed for postmortem histological verification of recording sites, whereby brains were removed, immediately placed in cryogenic compound (OCT), and frozen at −80 C for further cryosectioning. Serial sections (25 µm) were treated with cresyl violet and hematoxylin for viewing under light microscope.

For tonic and burst spike sorting, extracellular spike waveforms (action potentials) in VPL were detected and sorted from LFP waveforms, bandpass filtered at 300-3000 Hz, using primarily template matching and principle component algorithms in Spike2 (CED 1401, Cambridge Electronic Design, UK). Sorted spikes were then screened visually and inspected for false-positive or overlapping unitary assignments. Only one electrode per tetrode was used for spike sorting to minimize redundant assignments from the same unit. Hence, 3-4 units were isolated from VPL per mouse, whereas cortical oscillations reflected the mean of 3-4 LFP measurements in SI. Moreover, isolation of putative unitary spikes also met the criterion of inter-spike interval (ISI)>2 ms (refractory period). Burst analysis was performed on sorted spikes and others related to thalamic bursting evoked specifically by TRN stimulation, whereby burst events were identified according to the following parameters: maximum interval signifying burst onset=4 ms, offset=8 ms, longest increase in ISI within a burst=2 ms, and minimum number of spikes within a burst=2.

For optical stimulation of TRN, laser light pulses were generated using a 100 mW 473 nm laser (MBL473 Opto- Engine LLC) connected to the FlexDrive via fiber patch cord. Pulse control was achieved using an isolated pulse-generator (A-M systems 2100) at a 10 Hz frequency, 0.5 ms pulse width, and total duration of 5 sec during electrophysiological recording. For behavioral testing of the mechanical withdrawal threshold, optical stimulation was applied for 2 seconds during the application of von Frey filaments.

For acute and chronic pain models, capsaicin (0.1%, 10 µl, intradermal) was injected into the plantar aspect of the left hindpaw under sedation (1.5% isoflurane <2 min) to prevent stress due to restraining the hindpaw. A TRPV1 agonist, capsaicin causes increased neuronal firing of nociceptors, mainly polymodal C-fibers. Chronic constriction injury (CCI) was induced in the same mice that underwent capsaicin treatment at 3 days post-injection after verifying that mechanical withdrawal returned to normal. The sciatic nerve was exposed unilaterally after skin incision at the midthigh level and blunt dissection of the biceps femoris under deep anesthesia (isoflurane, 3.5%). Four chromic gut (5-0) ligatures were tied loosely around the nerve 1 mm apart and the overlying muscles and skin were closed in layers with 5-0 ETHILON® sutures.

Fast Fourier transform function (FFT) was used to convert LFP waveform from the time domain to the frequency domain, yielding power spectral density (PSD) histograms using 5 sec time intervals during awake resting state (no difference was found compared to the multi-taper method). Values were generated at 57 frequencies (0.47 Hz bins) between 3-30 Hz. For the pain state, data were collected within 15-20 min after capsaicin injection.

Mechanical sensitivity of the hindpaw was assessed by measuring the threshold of withdrawal in response to the application of calibrated von Frey filaments of different bending forces to the plantar aspect of the hindpaw according to the 'up-down' method, whereby filaments of different bending forces were pressed against the paw until buckling for a maximum of 3 seconds or a withdrawal reflex. This test represents naturally-occurring stimulation to the hindpaw in the noxious and non-noxious range evoking a biologically-relevant state in mammals.

In the dual chamber conditioned place preference (CPP) test, FlexDrive-implanted mice were conditioned with unrestricted access to both chambers for three days, with baseline preference determined on the third day. On the fourth day, mice underwent 'pairing' by being individually restricted to one chamber and receiving optical stimulation (10 Hz, 0.5 ms pulse width) for 30 sec, then 4 hours later they were restricted to the opposite chamber for 30 min after receiving optogenetic stimulation. On the fifth day, mice were allowed free access to both chambers. Chamber preference was video recorded and analyzed off-line by an observer blinded to the animal's treatment.

The distribution of the number of bursts and spikes in VPL per bin, and the magnitude of SI theta power per bin were analyzed for 919 bins for each mouse (n=5, bin size 30 ms). Regarding SI theta power, the mean observed power of 3 consecutive bins was used as the representative power of a bin (e.g. the average of the observed power of the bini-1, the bini, and the bini+1 was used as the representative power of the bini) to satisfy the conditions of accurate power estimation (100 ms bin size) and fine temporal resolution (30 ms bin size). Analysis revealed that both the number of bursts and spikes per bin had Poisson distribution and more than one burst or two spikes per bin were considered significant events. SI theta power per bin had a lognormal distribution.

The relationship between fluctuation of SI theta power and spikes or bursts was analyzed using cross-correlation analysis as described previously. Briefly:

$$Q(t)=1/(T-t)\Sigma_{i=1}^{T-t}X(i)Y(i+t)$$

Where, in the case of burst, X(i) was 1 (if there were any bursts in the bini) or 0 (if there was no burst in the bini), and in the case of spikes, X(i) was 1 (if there were more than two spikes and no burst in the bini) or 0 (otherwise). Y(i+t) represented the fluctuation of theta power with t bins lags from the bini, and was calculated as follows:

$$Y(i)=df(t)/di=\{f(i+1)-f(i)\}/\Delta t$$

Where f(i) represents "–log transformed S1 theta power at bini", and $\Delta i$ is the size of bini. If no relationship is found between bursts or spikes in VPL and fluctuation in SI power, Q(t) would have normal distribution. Thus, Z value was calculated for each Q(t) as follows:

$$Z(t)=\{Q(t)-E[Q(t)]\}/\sqrt{V[Q(t)]}$$

Where:

$$E[Q(t)]=E[X]E[Y]$$

And $$V[Q(t)]=1/(T-t)(E[X^2]E[Y^2]-E[X]^2E[Y]^2)$$

Z(t) was calculated for each mouse, and then, the average of Z(t) and the 95% confidence interval of Z(t) were calculated.

Analysis of variance (ANOVA) and parametric tests were used for statistical analysis. Two-way ANOVA analysis followed by Bonferroni's correction, Student's t-test, or the z-score method was used to compute statistical significance. Bartlett's test was performed to compute normal distribution and equal variance. A P value <0.05 was considered significant (denoted with * in figures). For behavioral and power data, comparisons were made between animal groups and for spike and burst activity data comparisons were made between neuronal groups. All values are reported as ±standard error of the mean (SEM).

Figure 9C:
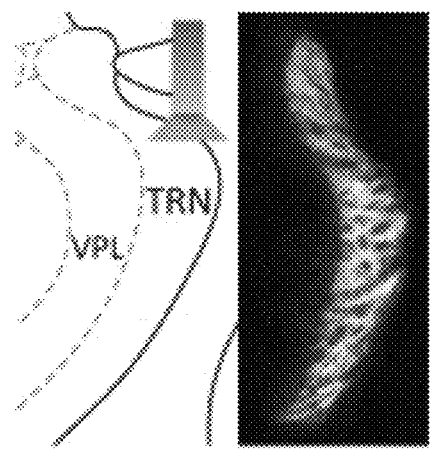
Figure 9D:
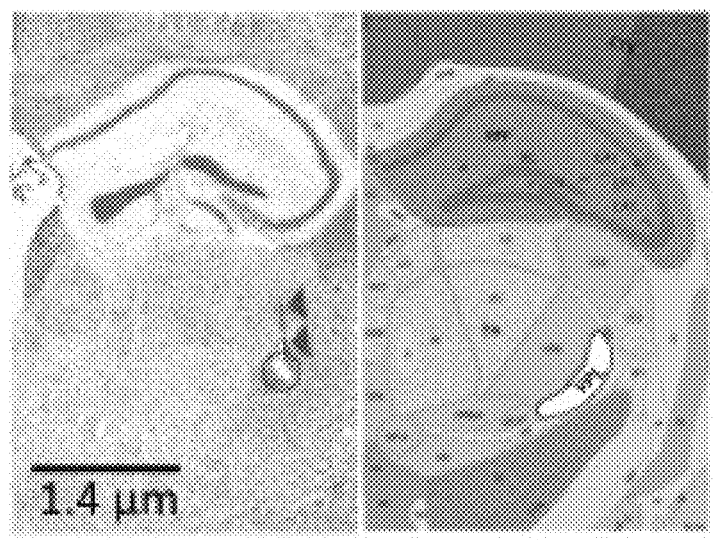
Figure 10A:
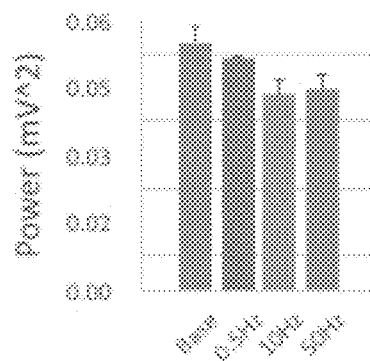
FIGS. 10A-10D are graphs showing that TRN stimulation decreases SI power in the theta band while increasing thalamic bursts and the withdrawal threshold in naïve VGAT mice. A histogram of the effects of TRN stimulation at 0.5, 10, and 50 Hz on mean theta (4-8 Hz) power under 1.5% isoflurane sedation is shown (n=2 mice.
Figure 10B:
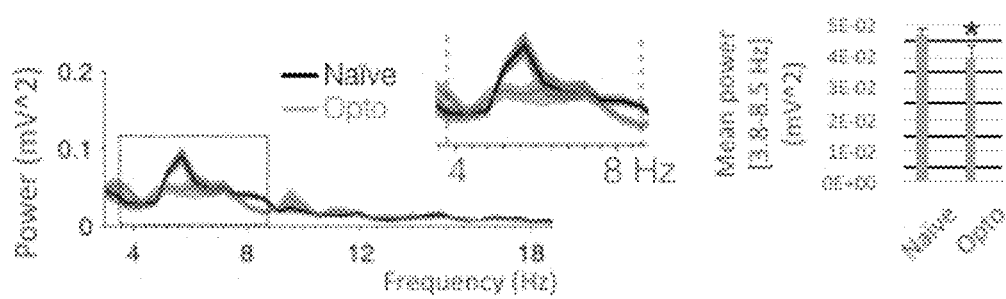
Figure 10C:
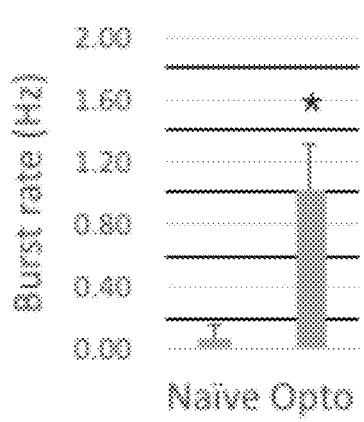
Figure 10D:
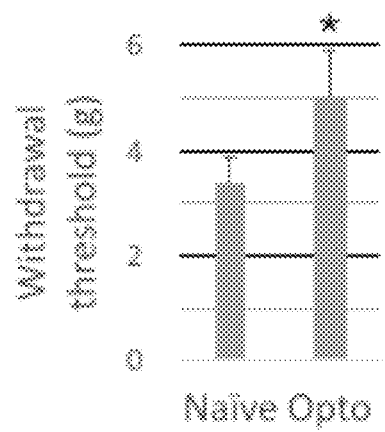

Example 10. Thalamic Bursts Down-Regulate Cortical Theta and Nociceptive Behavior Histological analysis confirmed that ChR2 expression was limited to GABAergic neurons in the TRN (FIGS. 9C-9D). Optical stimulation at 10 Hz, which is consistent with the physiological 'baseline' firing rate of TRNs, effectively reduced SI theta power in sedated mice (FIG. 10A). In particular, TRN stimulation at 0.5, 10, and 50 Hz reduced SI theta power to $5.14\times10^{-2}\pm710\times10^{-2}$ mV$^2$, $4.35\times10$-$2\pm0.33\times10^{-2}$ mV$^2$, and $4.45\times10$-$2\pm0.36\times10^{-2}$ mV$^2$, respectively, compared to the baseline SI theta power of $5.48\times10^{-2}\pm0.38$ mV$^2$. TRN stimulation at 10 Hz reduced power in awake, resting mice within the theta range of 3.8-8.5 Hz from $4.70\times10^{-2}\pm0.25\times10^{-2}$ mV$^2$ to $3.97\times10^{-2}\pm0.40\times10^{-2}$ mV$^2$ (FIG. 10B; P=0.033). Moreover, TRN stimulation increased the burst firing rate of putative single-units in VPL from 0.07±0.09 Hz to 1.01±0.31 Hz (FIG. 10C, P=0.002). This stimulation also enhanced the threshold of paw withdrawal to von Frey stimuli from 3.38±0.52 g to 5.02±0.88 g (FIG. 10D; P=0.03). These results show that rescue of TRN function by selective optical stimulation releases thalamic neurons from inhibition, and thus, promotes thalamic bursting, reduces cortical theta, and reverses nociceptive behavior.

Figure 11A:
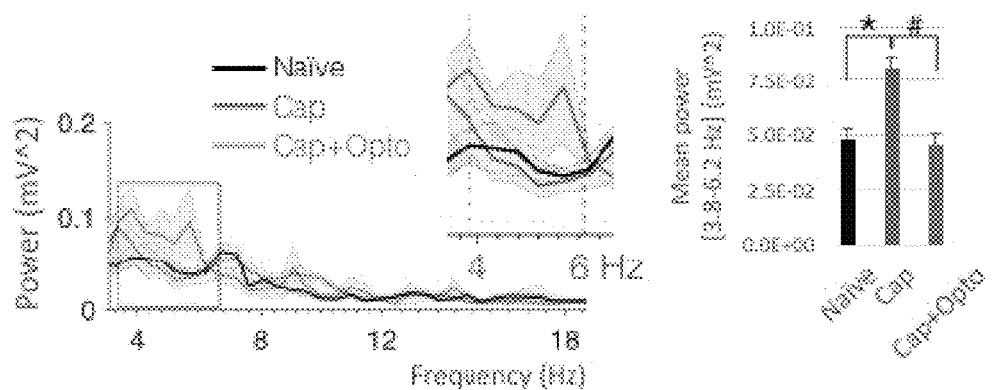
FIGS. 11A-11E are graphs showing that TRN stimulation during acute pain rescues SI theta power and reverses allodynia. SI power spectra are shown, in which the right panel inset shows increased power within the theta band (3.8-6.2 Hz) following capsaicin compared to naïve mice, whereas TRN stimulation reverses these changes (n=5 mice.
Figure 11B:
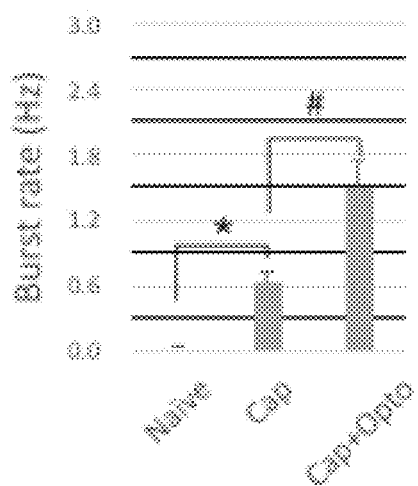
Figure 11C:
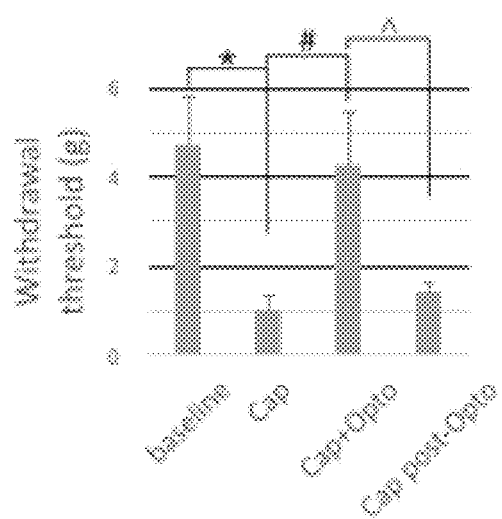

Next, the effect of TRN stimulation on thalamic firing was investigated in a pain model. SI power increased significantly in the theta band within 15-20 minutes after intradermal injection of capsaicin in the hindpaw from $4.82 \times 10^{-2} \pm 0.57 \times 10^{-2}$ mV$^2$ to $8.15 \times 10^{-2} \pm 0.13 \times 10^{-2}$ mV$^2$ at 3.8-6.2 Hz (FIG. 11A; P=0.048). In these mice, TRN stimulation effectively reversed the pain-related increase in SI power to normal levels from $8.15 \times 10^{-2} \pm 0.13 \times 10^{-2}$ mV$^2$ to $4.55 \times 10^{-2} \pm 0.75 \times 10^{-2}$ mV$^2$ (FIG. 3a; P=0.002). The rate of spontaneous burst firing in VPL neurons (0.02±0.02) increased after capsaicin injection (0.64±0.11) and was further enhanced during TRN stimulation (1.50±0.25) in the same neurons (FIG. 11B; *P=0.00002, *P=0.001). Paw withdrawal threshold decreased within 15-20 minutes after capsaicin injection from 4.47±1.07 g to. 1.00±0.37 g suggesting mechanical allodynia, which is a hallmark of neuropathic pain (FIG. 11C; *P=0.011). Optical TRN stimulation, however, elevated withdrawal thresholds to near pre-capsaicin levels of 4.28±1.22 (FIG. 11C; *P=0.023). Reversal of these anti-nociceptive effects to 1.41±0.22 occurred within 5 min afterwards (FIG. 11C; *P=0.048). We further investigated the longitudinal effects of TRN stimulation on thalamic firing, theta power, and nociceptive behavior following chronic constriction injury (CCI) of the sciatic nerve in the same animals. The results of these studies are comparable overall to those obtained in the capsaicin pain model.

Figure 11D:
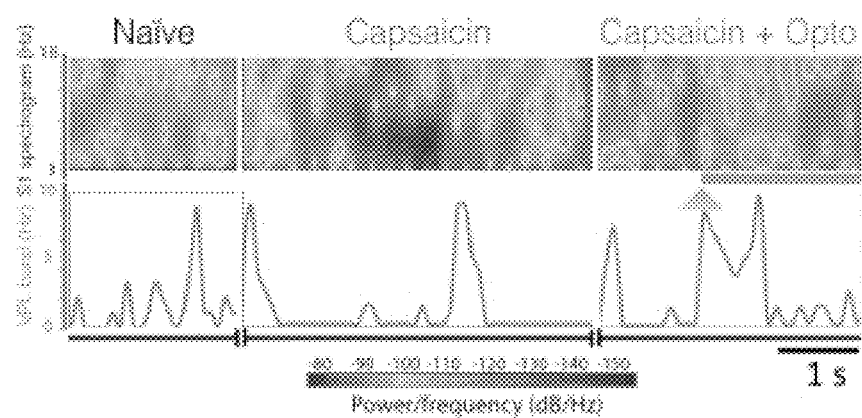
Figure 11E:
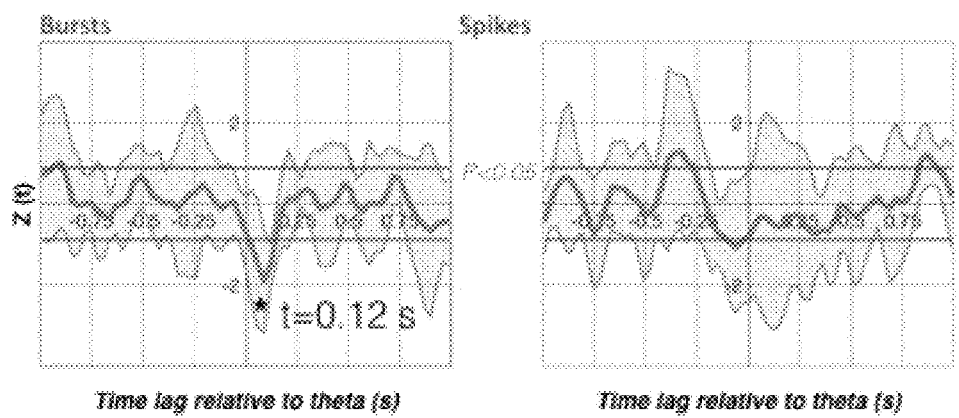

The temporal relationship between thalamic firing and cortical theta was then investigated. As shown in a representative example of a time series of SI spectrogram with corresponding VPL burst rate, epochs of high theta power and burst events do not coincide temporally (FIG. 11D). Dynamic, time-lagged cross-correlation between burst or tonic firing rate versus theta power revealed a significantly negative correlation between theta amplitude and burst rate, which suggests that bursts (but not tonic firing) likely trigger the down-regulation of SI theta with a time lag of 120 ms (FIG. 11E).

Promotion of burst firing in thalamocortical neurons during naïve and pain states is negatively correlated with cortical theta and mechanical allodynia. Our data show that optogenetically-induced thalamic bursts attenuate pain-induced cortical oscillations and enhance withdrawal threshold to mechanical stimuli. These results indicate that thalamic bursts are an adaptive response to pain that de-synchronizes cortical theta and decreases sensory salience. Optogenetic stimulation of the thalamic reticular nucleus promotes burst firing in the thalamus while down-regulating theta oscillations in the somatosensory cortex and attenuating pain behavior.

OTHER EMBODIMENTS

Various modifications and variations of the described methods will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method for detecting pain in a subject, the method comprising:
    (a) recording theta or gamma waveforms in a somatosensory cortex or a frontal cortex of the subject by electroencephalography (EEG);
    (b) applying fast Fourier transfer (FFT) to convert the waveforms from the time domain to the frequency domain, thereby producing power spectral density (PSD); and
    (c) determining power amplitude from the PSD, wherein an increase in the power amplitude in a theta or gamma frequency band in the somatosensory cortex or the frontal cortex relative to baseline serves as an indicator of pain.

2. A method for detecting pain in a subject, the method comprising:
    (a) recording theta or gamma waveforms in a somatosensory cortex or a frontal cortex of the subject by EEG;
    (b) applying FFT to convert the waveforms from the time domain to the frequency domain, thereby producing PSD;
    (c) determining power amplitude from the PSD; and
    (d) determining coherence of brain regions from the FFT, wherein an increase in the power amplitude in a theta or gamma frequency band in the somatosensory cortex or the frontal cortex relative to baseline and an increase in the coherence of brain regions serve as an indicator of pain.

3. The method of claim 2, wherein the coherence of brain regions is determined from the difference in coherence at individual frequency units or frequency bands.

4. The method of claim 1, further comprising stimulating a thalamic reticular nucleus (TRN) of the subject if an increase in power amplitude is detected.

5. The method of claim 4, wherein the TRN is stimulated with a laser-emitting optic fiber adapted for implantation in the brain of the subject or a therapeutic agent.

6. The method of claim 1, wherein the waveforms are theta waveforms.

7. The method of claim 1, wherein the waveforms are gamma waveforms.

8. The method of claim 1, wherein the waveforms are theta and gamma waveforms.

9. The method of claim 1, wherein step (a) comprises recording in the somatosensory cortex.

10. The method of claim 1, wherein step (a) comprises recording in the frontal cortex.

11. The method of claim 1, wherein step (a) comprises recording in the somatosensory cortex and the frontal cortex.

12. The method of claim 1, wherein the power amplitude from the PSD is determined in the theta frequency band.

13. The method of claim 1, wherein the power amplitude from the PSD is determined in the gamma frequency band.

14. The method of claim 1, wherein the power amplitude from the PSD is determined in the theta and gamma frequency bands.

15. The method of claim 1, wherein the power amplitude from the PSD is determined in the somatosensory cortex.

16. The method of claim 1, wherein the power amplitude from the PSD is determined in the frontal cortex.

17. The method of claim 1, wherein the power amplitude from the PSD is determined in the somatosensory cortex and frontal cortex.

* * * * *